US009493507B2

(12) United States Patent
Mograbi

(10) Patent No.: US 9,493,507 B2
(45) Date of Patent: Nov. 15, 2016

(54) GLUTATHIONE-ELEVATING COMPOSITIONS AND USES THEREOF

(71) Applicant: Oneday— Biotech And Pharma Ltd., Tel Aviv (IL)

(72) Inventor: Josef Mograbi, Tel Aviv (IL)

(73) Assignee: ONEDAY—BIOTECH AND PHARMA LTD., Tel Aviv (IL)

( * ) Notice: Subject to any disclaimer, the term of this patent is extended or adjusted under 35 U.S.C. 154(b) by 0 days.

(21) Appl. No.: 14/603,770

(22) Filed: Jan. 23, 2015

(65) Prior Publication Data

US 2015/0133386 A1    May 14, 2015

Related U.S. Application Data

(63) Continuation of application No. PCT/IL2013/050623, filed on Jul. 22, 2013.

(60) Provisional application No. 61/674,403, filed on Jul. 23, 2012.

(51) Int. Cl.
 *A61K 38/07* (2006.01)
 *A61K 38/08* (2006.01)
 *C07K 5/103* (2006.01)

(52) U.S. Cl.
 CPC ............. *C07K 5/1013* (2013.01); *A61K 38/07* (2013.01)

(58) Field of Classification Search
 CPC ..... A61K 38/07; A61K 38/08; C07K 5/1013
 USPC ........................................................ 514/13.5
 See application file for complete search history.

(56) References Cited

U.S. PATENT DOCUMENTS

| | | | |
|---|---|---|---|
| 4,585,735 A | 4/1986 | Meryman et al. | |
| 4,812,310 A | 3/1989 | Sato et al. | |
| 4,966,848 A | 10/1990 | Smith et al. | |
| 5,147,776 A | 9/1992 | Koerner, Jr. | |
| 5,223,421 A | 6/1993 | Smith et al. | |
| 5,248,506 A | 9/1993 | Holme et al. | |
| 5,250,303 A | 10/1993 | Meryman et al. | |
| 5,789,151 A | 8/1998 | Bitensky et al. | |
| 5,837,218 A | 11/1998 | Peers et al. | |
| 5,874,468 A | 2/1999 | Atlas et al. | |
| 5,889,055 A | 3/1999 | Howard | |
| 5,928,926 A | 7/1999 | Kurdi-Haidar et al. | |
| 5,985,261 A | 11/1999 | White et al. | |
| 6,267,925 B1 | 7/2001 | Pages | |
| 6,369,106 B1 | 4/2002 | Atlas et al. | |
| 6,527,957 B1 | 3/2003 | Deniega et al. | |
| 6,627,746 B1 | 9/2003 | Doberstein et al. | |
| 6,770,478 B2 | 8/2004 | Crowe et al. | |
| 6,903,136 B2 | 6/2005 | Miller et al. | |
| 7,195,766 B2 | 3/2007 | White | |
| 7,307,063 B2 | 12/2007 | Sharma et al. | |
| 7,534,438 B2 | 5/2009 | White | |
| 8,735,343 B2 | 5/2014 | White | |

| | | |
|---|---|---|
| 2006/0057188 A1 | 3/2006 | Gaetani |
| 2007/0033666 A1 | 2/2007 | Harris et al. |
| 2008/0009448 A1 | 1/2008 | Sakurada |
| 2008/0069839 A1 | 3/2008 | Guan et al. |
| 2009/0156508 A1 | 6/2009 | Schteingart et al. |
| 2009/0285912 A1 | 11/2009 | Rodriquez |
| 2011/0318380 A1 | 12/2011 | Brix et al. |

FOREIGN PATENT DOCUMENTS

| | | |
|---|---|---|
| WO | 9533765 A1 | 12/1995 |
| WO | 99/62927 A1 | 12/1999 |
| WO | 0234202 A2 | 5/2002 |
| WO | 0299084 A2 | 12/2002 |
| WO | 2004024868 A2 | 3/2004 |
| WO | 2004111636 A2 | 12/2004 |
| WO | 2005075679 A2 | 8/2005 |
| WO | 2005123108 A2 | 12/2005 |
| WO | 2010037395 A2 | 4/2010 |
| WO | 2012098546 A2 | 7/2012 |
| WO | 2014016837 A1 | 1/2014 |

OTHER PUBLICATIONS

N-acetylcysteine from http://www.naturalremedies.org/n-acetylcysteine/, pp. 1-6. Accessed Feb. 1, 2016.*
Amer et al., (2005) Red blood cells, platelets and polymorphonuclear neutrophils of patients with sickle cell disease exhibit oxidative stress that can be ameliorated by antioxidants. British Journal of Haematology 132(1): 108-113.
Amer et al., (2008) N-acetylcysteine amide (AD4) attenuates oxidative stress in beta-thalassemia blood cells. Biochim Biophys Acta 1780(2): 249-55.
Bachnoff et al., (2011) Alleviation of oxidative stress by potent and selective thioredoxin-mimetic peptides. Free Radic Biol Med 50(10): 1355-67.
Ballatori et al., (2009) Glutathione dysregulation and the etiology and progression of human diseases. Biol Chem 390(3): 191-214.
Banerjee (2009) Hemolytic uremic syndrome. Indian Pediatr 46(12): 1075-84.
Bartov et al., (2006) Low molecular weight thiol amides attenuate MAPK activity and protect primary neurons from Aβ (1-42) toxicity. Brain Res 1069(1): 198-206.

(Continued)

*Primary Examiner* — Julie Ha
(74) *Attorney, Agent, or Firm* — Vorys, Sater, Seymour & Pease LLP

(57) ABSTRACT

Use of synthetic thiol-containing peptides as highly effective therapeutic and protective agents is described, in clinical and research applications where lifespan and/or viability and functioning of cells is compromised at least partially due to depletion of reduced glutathione, or where viability and functioning of cells can be improved by elevating reduced glutathione levels. More specifically, compositions and methods for treating blood disorders associated with glutathione dysregulation utilizing short thiol-containing peptides selected from the group consisting of Cys-Lys-Met-Cys (SEQ ID NO: 1), Cys-Met-Lys-Cys (SEQ ID NO: 2) and Cys-β-Ala-His-Cys (SEQ ID NO: 3) are described. Further described are compositions and methods for preserving biological samples using the peptides.

23 Claims, 8 Drawing Sheets

(56) References Cited

OTHER PUBLICATIONS

Batt and Reske (2010) The Hospital Physician® Board Review Manuals, Hematology, vol. 5, Part 3 pp. 1-12, Hemoglobinopathies, published by Turner White Communications, Inc.
Behrends et al., (1996) Evaluation of the secondary structure of vaccinia-virus thymidine kinase by circular-dichroism spectroscopy of overlapping synthetic peptides. Eur J Biochem 241(1): 126-132.
Bolton-Maggs et al., (2004) Guidelines for the diagnosis and management of hereditary spherocytosis. Br J Haematol 126(4): 455-74.
Breuer et al., (2012) Non-transferrin bound iron in Thalassemia: differential detection of redox active forms in children and older patients. Am J Hematol 87(1): 55-61.
Cacciatore et al., (2010) Prodrug approach for increasing cellular glutathione levels. Molecules 15(3): 1242-64.
Chassaing et al., (1999) Determination of reduced and oxidized homocysteine and related thiols in plasma by thiol-specific pre-column derivatization and capillary electrophoresis with laser-induced fluorescence detection. J Chromatogr B Biomed Sci Appl 735(2): 219-27.
Fibach (1998) Techniques for studying stimulation of fetal hemo-globin production in human erythroid cultures. Hemoglobin 22(5-6): 445-58.
Fibach and Rachmilewitz (2008) The role of oxidative stress in hemolytic anemia. Curr Mol Med 8(7): 609-19.
Fibach et al., (2010) Amelioration of oxidative stress in red blood cells from patients with beta-thalassemia major and intermedia and E-beta-thalassemia following administration of a fermented papaya preparation. Phytother Res 24(9): 1334-8.
Fraternale et al., (2009) GSH and analogs in antiviral therapy. Mol Aspects Med 30(1-2): 99-110.
Gallagher (2004) Hereditary elliptocytosis: spectrin and protein 4.1R. Semin Hematol 41(2): 142-64.
Gehrs and Friedberg (2002) Autoimmune hemolytic anemia. Am J Hematol 69(4): 258-71.
Grinberg et al., (2005) N-acetylcysteine amide, a novel cell-perme-ating thiol, restores cellular glutathione and protects human red blood cells from oxidative stress. Free Radic Biol Med 38(1): 136-45.
Hess (2006) An update on solutions for red cell storage. Vox Sang 91(1): 13-9.
Hudson (2001) Rethinking cystic fibrosis pathology: the critical role of abnormal reduced glutathione (GSH) transport caused by CTFR mutation. Free Radic Biol Med 30(12): 1440-61.
Kim et al., (2011) A novel dithiol amide CB3 attenuates allergic airway disease through negative regulation of p38 mitogen-acti-vated protein kinase. Am J Respir Crit Care Med 183(8):1015-1024.
Kohne (2011) Hemoglobinopathies: clinical manifestations, diag-nosis, and treatment. Dtsch Arztebl Int 108(31-32): 532-40.
Koren et al., (2008) Response to hydroxyurea therapy in beta-thalassemia. Am J Hematol 83(5): 366-70.

Mingshan et al., (2008) Endoplasmic Reticulum Stress and Unfolded Protein Response in Atm-Deficient Thymocytes and Thy-mic Lymphoma Cells Are Attributable to Oxidative Stress1. Neoplasia 10(2): 160-167.
Owen and Butterfield (2010) Measurement of oxidized/reduced glutathione ratio. Methods Mol Biol 648: 269-77.
Tiwari et al., (2009) Radiation-induced micronucleus formation and DNA damage in human lymphocytes and their prevention by antioxidant thiols. Mutat Res 676(1-2): 62-68.
Townsend et al., (2003) The importance of glutathione in human disease. Biomed Pharmacother 57(3-4): 145-55.
Withers and King (1979) Proline: A Novel Cryoprotectant for the Freeze Preservation of Cultured Cells of *Zea mays* L. Plant Physiol 64(5): 675-8.
Wu et al., (2004) Glutathione metabolism and its implications for health. J Nutr 134(3): 489-92.
M. Galvani, et al.; "The Role of Carnitine System in Maintaining Muscle Homeostasis" Basic Appl Myol vol. 13, No. 3.; 2003; pp. 105-120.
A. Clay, et al.; "Mitochondrial Disease—A Pulmonary and Critical-Care Medicine Perspective" Chest, vol. 120, No. 2; Aug. 2001; 633-649.
J. Flanagan, et al.; :Role of Carnitine in Disease; Nutrition and Metabolism, vol. 7, No. 30; <http://www.nutritionandmetabolism.com/content/7/1/30>; 2010; pp. 1-14.
W. Hiatt, et al.; "Carnitine and Acylcarnitine Metabolism During Exercise in Humans"; The American Society for Clinical Investi-gation, Inc., vol. 84, Oct. 1989; pp. 1167-1173.
M. Krajcovicova-kudlackova, et al.; "Correlation of Carnitine Lev-els to Methionine and Lysine Intake" Physiol. Res.; 2000; pp. 399-402.
W-C. Liang; "State of the Art in Muscle Lipid Diseases"; Acta Myologica; vol. XXIX; 2010; pp. 351-356.
W. Liang, et al.; "Lipd Storage Myopathy"; Curr eurol Neurosci Rep, vol. 11; 2011; pp. 97-103.
MDA; "Facts About Mitochondrial Myopathies" Mitochondrial Myopathies; 2011; pp. 1-15.
J.R. Terrill, et al.; "N-Acetylcysteine Treatment of dystrophic mdx mice results in protein thiol modifications and inhibition of exercise induced myofibre necrosis"; Neuromuscular Disorders; Elsevier B.V.; 2011; pp. 1-8.
F. Vaz, et al.; "Carnitine Biosynthesis in mammals"; Biochem Journal, vol. 316; Great Britain; 2002; pp. 417-429.
Lu et al., (2009) Regulation of glutathione synthesis. Mol Aspects Med 30(1-2): 42-59.
Vitamin C from http://www.globalhealingcenter.com/natural-health/foods-high-in-vitamin-c/, pp. 1-3. Accessed Feb. 1, 2016.
Q85485 from UniProt, pp. 1-3. Sequence updated on Nov. 1, 1996. Accessed Mar. 26, 2016.
A0A078CKJ2 from UniProt, pp. 1-3. Sequence updated on Oct. 29, 2014. Accessed Mar. 26, 2016.

* cited by examiner

GLUTATHIONE-ELEVATING COMPOSITIONS AND USES THEREOF

FIELD OF THE INVENTION

The present invention relates to compositions that elevate the levels of reduced glutathione in cells and tissues and uses thereof. More specifically, the present invention relates to the use of short thiol-containing peptides in the treatment of blood disorders characterized by glutathione dysregulation, and in preservation of biological samples.

BACKGROUND OF THE INVENTION

Blood disorders are medical conditions which affect one or more components of the blood, including red blood cells, white blood cells and platelets.

For example, hemoglobinopathies are a group of inherited blood disorders involving defective hemoglobin (Hb) production. The different hemoglobinopathies fall into two main groups: thalassemia syndromes, characterized by reduced synthesis of globin subunits that are structurally normal, and structural hemoglobin variants (abnormal hemoglobins) syndromes, characterized by the synthesis of structurally abnormal globin subunits. Both groups are caused by mutations and/or deletions in the globin related genes. Some hemoglobinopathies are mixed forms that combine features of the two main groups. The most common clinical manifestations of hemoglobinopathies include anemia of variable severity and variable pathophysiology.

In the thalassemia syndromes, which are autosomal recessive conditions, the decrease in globin chain production may result from gene deletion or mutations that adversely affect the transcription or stability of mRNA products. The main types of thalassemia are α-thalassemia, which results from a deletion or mutation in one or more of the four α-globin genes, and β-thalassemia, which results from a deletion or mutation in one or more of the two β-globin genes.

The main two types of thalassemia are further classified based on their severity and the number of gene copies that are affected. β-thalassemia includes β-thalassemia minor (also called (β-thalassemia trait), intermedia and major (also called Cooley's anemia). Generally, if one β-globin gene is affected, thalassemia minor is the result. If the two (β-globin genes are affected, the result is thalassemia intermedia or major, depending on how severely the gene is affected. The genes can be mutated or even completely deleted.

α-thalassemia includes a silent carrier state, where one gene is affected, α-thalassemia trait, where two genes are affected, hemoglobin H disease, where three genes are affected, and α-thalassemia major (also called Hb Bart's hydrops fetalis), where four genes are affected. The latter is a sever condition typically diagnosed in utero, and fetuses with α-thalassemia major are usually miscarried, stillborn, or die shortly after birth.

In addition to decreased hemoglobin production, manifestations of the thalassemias are complicated by the resulting chain imbalance: in α-thalassemia, the β- and/or γ-globin chains are produced in excess. Similarly, in β-thalassemia, α-chains are produced in excess. Hemoglobin chain imbalance damages, shortens life span, and sometimes even destroys red blood cells, leading to anemia.

In the structural hemoglobin variants syndromes, which are autosomal dominant conditions, the structural defects of the globin chains result from an altered amino acid sequence in the α or β chains. Hundreds of hemoglobin variants have been hitherto described, the majority of which are clinically benign or negligible. Some, however, are associated with pathology. The clinically significant variants are divided into four groups. The first group includes variants with a tendency to aggregate, which are associated with sickle cell syndromes, e.g. the HbS variant. The point mutation in the β-globin gene that produces HbS exerts its effect by causing precipitation and polymerization of the HbS with resulting sickling of the red cells. These sickled cells lack deformability, occlude the microvasculature, and lead to necrosis and tissue infarctions, which manifest as painful sickle cell crises. The permanently deformed cells are subsequently removed from the circulation well before the usual 120-day life span of a healthy red cell, contributing to a chronic non-hemolytic and/or hemolytic anemia. The clinical manifestations generally occur only in individuals with homozygous sickle cell disease.

The second group of Hb variants includes variants with abnormal hemoglobin synthesis, e.g. HbE. The third group includes variants with a tendency to precipitate, which are associated with hemolysis (fragile red blood cells), e.g. Hb Köln. The fourth group includes variants with abnormal oxygen transportation and congenital polycythemia, e.g. Hb Johnstown, or with congenital cyanosis (abnormal methemoglobins, HbM abnormalities, e.g. M-Iwate).

Treatment of the different hemoglobinopathies depends on the severity of the disease. For example, hematopoietic stem-cell transplantation is the preferred treatment for the severe forms of thalassemia. Supportive, rather than curative, treatment includes periodic blood transfusions for life, combined with iron chelation. Drugs to treat the symptoms of sickle-cell disease include analgesics, antibiotics, corticosteroids, ACE inhibitors and hydroxyurea.

A growing body of experimental and clinical evidence point to the important role played by oxidative stress in hemoglobinopathies. For example, it has been shown previously that blood cells derived from patients with β-thalassemia and sickle cell anemia, including red blood cells (RBC), platelets and polymorphonuclear neutrophils (PMN), are under oxidative stress—their reactive oxygen species (ROS) were higher than normal and their reduced glutathione (GSH) level was lower than normal. Oxidative stress in thalassemia is thought to be caused primarily by the RBC abnormalities, namely, degradation of unstable Hb which results in free globin chains and heme. Another contributing factor is iron overload due to increased intestinal absorption and therapeutic blood transfusions. Several studies indicated the presence of elevated levels of free radicals, as well as iron-containing compounds, probably released from damaged RBC, in thalassemic plasma.

Oxidative stress in hemoglobinopathies may explain clinical symptoms, for example, the anemia due to the short survival of mature RBC in the circulation. The oxidative stress of platelets could account for their increased tendency to undergo activation and aggregation and the high incidence of thromboembolic complications in these patients. The chronic oxidative stress of the PMN may result in ineffective bactericidal activity which may cause recurrent infections.

An additional blood disorder known to be associated with oxidative stress is hemolytic uremic syndrome (HUS). HUS is a condition that results from an abnormal premature destruction of red blood cells. It often occurs following a gastrointestinal infection with *Escherichia coli*, which produces toxic substances that destroy the cells. The condition has also been linked to other gastrointestinal infections, including *Shigella* and *Salmonella*, as well as non-gastrointestinal infections and other factors such as adverse drug reaction and drug overdose. The damaged red blood cells usually clog the filtering system in the kidneys, which may eventually cause a life-threatening kidney failure. Treatment of HUS may include fluid replacement, RBC transfusions, platelet transfusions, plasma exchange, kidney dialysis, and medications such as corticosteroids.

HUS was found to involve changes in RBCs lipid peroxidation, reduced glutathione (GSH) levels and impaired metabolism, reduced antioxidant enzyme activities (catalase, superoxide dismutase, glutathione peroxidase) and abnormal hemoglobin metabolites' levels. It has been suggested that in the acute phase of HUS, RBCs are exposed to an oxidative stress that could contribute to hemolysis directly through oxidative damage and/or by membrane permeability and impaired membrane fluidity.

Another disorder known to be associated with reduced GSH levels, oxidative stress and destruction of red blood cells is glucose-6-phosphate dehydrogenase (G6PD) deficiency. G6PD deficiency is an X-linked recessive hereditary disease characterized by abnormally low levels of the enzyme glucose-6-phosphate dehydrogenase. This enzyme is a metabolic enzyme involved in the pentose phosphate pathway, which is particularly important in red blood cell metabolism. G6PD also plays an important role in the production of reduced nicotinamide adenine dinucleotide phosphate (NADPH). NADPH is necessary for the regeneration of reduced glutathione through reducing oxidized glutathione (GSSG). G6PD deficient red blood cells are therefore highly vulnerable to oxidative damage and tend to hemolyze.

The most frequent clinical manifestations of G6PD deficiency include neonatal jaundice, acute hemolytic anemia and favism, which is usually triggered by exogenous agents e.g. toxins, oxidants and certain food, most notably fava beans. Some G6PD variants cause chronic hemolysis. The most effective management of G6PD deficiency is avoidance of drugs or substances known to initiate hemolysis in G6PD deficiency patients.

Thus, effective compositions and methods for treating blood disorders associated with decreased levels of reduced glutathione (GSH) and/or oxidative stress, are needed.

Another exemplary condition where oxidative stress is thought to play a role and contribute to destruction or damaging of cells is preservation of biological samples.

For example, blood samples obtained from individuals are typically processed and stored until needed for use (transfusions and/or fractionation). Either whole blood or processed blood products, including for example red blood cell concentrates (packed red blood cells) and platelet concentrates, are stored under conditions aimed at preserving optimal viability and functioning during the maximum allowed storage period. For example, red blood cells are typically stored in a citrate-phosphate-dextrose (CPD) and/or saline-adenine-glucose-mannitol (SAGM) solution, at 2-8° C. Platelets are typically stored at 20-24° C. with sufficient non-stop agitation to permit good oxygenation and prevent aggregation.

In general, additive solutions for preservation of blood contain anticoagulants, sugars as an energy source, inorganic salts as agents for adjusting pH and osmotic pressure, and adenine as an agent for preventing consumption of blood ATP (adenosine triphosphate), ADP (adenosine diphosphate) and AMP (adenosine monophosphate). In addition to CPD and SAGM noted above, other known additive solutions include mannitol-adenine-phosphate (MAP) and phosphate-adenine-glucose-guanosine-saline-mannitol (PAGGSM).

However, even under current optimal storage conditions, modifications and/or degradation of blood components occur in the samples. These alterations, known as "storage lesions", affect lifespan and quality of the stored blood products.

Red blood cells, for example, undergo biochemical changes, such as reduction in the levels of GSH, ATP, which is necessary for multiple cellular processes, and 2,3-diphosphoglycerat (2,3-DPG), which is important for oxygen release. Biomechanical changes also occur, such as altered shape, deformability, aggregability, flexibility and intracellular viscosity. Protein modifications resulting from oxidative stress and progressive hemolysis are also observed. The storage period of red blood cells is currently limited for about 5-7 weeks under optimal conditions. Platelet storage lesions typically include reduction in the levels of GSH, morphological changes, platelet activation and platelet proteolysis. Their storage period is currently limited for up to 5 days under optimal conditions.

Improved compositions and methods for storing biological material, such as red blood cells, for extended periods of time, while maintaining their functionality and viability are needed.

Thiol (—SH) containing compounds are a type of molecules capable of neutralizing several types of damaging oxidative species, thus acting as reducing reagents. The activity of this group of compounds is mainly due to the sulfur atom they comprise which participates in nucleophilic attack on toxic electrophiles, scavenging free radicals, effecting repair of damaged targets through hydrogen atom donation, altering the redox status of the cell, or affecting gene transcription or protein function.

Thiol containing compounds include natural molecules, produced by all living organisms including animals and plants, as well as synthetic molecules. Examples of natural thiol containing antioxidants include reduced glutathione, which is one of the most potent and important antioxidants in mammals, thioredoxins and cysteine.

Examples of synthetic thiol containing redox molecules include N-acetylcysteine amide. Grinberg et al. (2005) *Free Radic Biol Med*, 38(1); 136-145 tested N-acetylcysteine amide for its antioxidant and protective effects using human red blood cells as a model.

Amer et al. (2008) *Biochim. Biophys. Acta*, 1780(2):249-55 describe in vitro and in vivo effects of N-acetylcysteine amide as an antioxidant in blood cells of β-thalassemic mice and patients WO 2002/034202 discloses an antioxidant compound characterized by (a) a peptide including at least three amino acid residues of which at least two are cysteine residues, each having a readily oxidizable sulfhydryl group for effecting antioxidation; and at least two peptide bonds, each being cleavable by at least one intracellular peptidase; and (b) a first hydrophobic or non-charged moiety being attached to an amino terminal of the peptide via a first bond and a second hydrophobic or non-charged moiety being attached to a carboxy terminal of the peptide via a second bond, the first hydrophobic or non-charged moiety and the second hydrophobic or non-charged moiety are selected so as to provide the antioxidant compound with membrane miscibility properties for permitting the antioxidant compound to cross cellular membranes; wherein cleavage of the at least two peptide bonds by the at least one intracellular peptidase results in generation of a plurality of antioxidant species, each including one of the cysteine residues having the readily oxidizable sulfhydryl group and which is also active in effecting antioxidation, thereby providing for a plurality of different antioxidant species acting in synergy in exerting antioxidation.

WO 2012/098546, to the inventor of the present invention and others, discloses potent compounds having combined antioxidant, anti-inflammatory, anti-radiation and metal chelating properties. Short peptides having said properties and methods and uses of such short peptides in clinical and cosmetic applications are disclosed. Among other peptides, Cys-Lys-Met-Cys (SEQ ID NO: 1), Cys-Met-Lys-Cys (SEQ ID NO: 2) and Cys-β-Ala-His-Cys (SEQ ID NO: 3) are disclosed.

There still remains a need for more effective and/or safer compositions and methods that may be useful to meet the above described needs.

SUMMARY OF THE INVENTION

The present invention is directed to the use of synthetic thiol-containing peptides as therapeutic and protective agents for preserving viability and functioning of blood, blood components, cells and organs more effectively than previously achieved with known peptides. These thiol-containing peptides are useful in therapeutic and protective agents in clinical and research applications where viability and functioning of blood, blood components, cells and organs is compromised at least partially due to depletion of reduced glutathione levels, or where viability and functioning of blood, blood components, cells and organs can be improved by elevating reduced glutathione levels. Applications amenable to treatment with the peptides of the invention include blood disorders characterized by an imbalanced ratio between reduced and oxidized glutathione (GSH: GSSG) within blood cells, and preservation of biological samples.

The highly potent peptide compounds utilized herein comprise unique dipeptide sequences situated between two cysteine amino acid residues, i.e. flanked by a cysteine residue on either end of the dipeptide sequence, optionally further comprising N- and C-terminal modifications. As disclosed herein for the first time, it was found that these peptides are capable of elevating GSH levels and/or balancing the GSH:GSSG ratio in favor of reduced glutathione, and alleviating oxidative stress within cells. Without being bound by any particular theory or mechanism of action, it is contemplated that balanced GSH:GSSG ratio improves at least some of the clinical manifestations of the blood disorders specified herein. It is further contemplated that balanced GSH:GSSG ratio promotes sustained viability and functioning of preserved cells and tissues.

In some embodiments, the amino and carboxy termini of the peptides are blocked by appropriate blocking groups. Suitable amino terminal blocking groups include, but are not limited to, acetyl, alkyl and acyl. Suitable carboxy terminal blocking groups include, but are not limited to, amide, ester and alcohol. Blocking groups exemplified herein include N-acetyl and C-terminal amide groups.

According to one aspect, the present invention provides a method for treating a blood disorder associated with glutathione dysregulation in a subject in need thereof, the method comprising administering to the subject a pharmaceutical composition comprising as an active ingredient at least one peptide or a salt thereof having an amino acid sequence selected from the group consisting of:

Cys-Lys-Met-Cys; (SEQ ID NO: 1)

Cys-Met-Lys-Cys; (SEQ ID NO: 2)
and

Cys-β-Ala-His-Cys. (SEQ ID NO: 3)

According to another aspect, the present invention provides a pharmaceutical composition comprising as an active ingredient at least one peptide or a salt thereof having an amino acid sequence selected from the group consisting of:

Cys-Lys-Met-Cys; (SEQ ID NO: 1)

Cys-Met-Lys-Cys; (SEQ ID NO: 2)
and

Cys-β-Ala-His-Cys, (SEQ ID NO: 3)

for use in the treatment of blood disorders associated with glutathione dysregulation.

In some embodiments, the disorders are characterized by poor functionality and low quality of red blood cells.

In some embodiments, the disorders are manifested by hemolytic anemia, with premature destruction of red blood cells.

In some embodiments, the disorder is selected from the group consisting of an intrinsic abnormality of red blood cells and a disorder extrinsic to red blood cells. Each possibility represents a separate embodiment of the invention.

In some embodiments, an intrinsic abnormality of red blood cells is selected from the group consisting of a red blood cell membrane disorder, a disorder of hemoglobin production (hemoglobinopathy), either qualitative impairment of hemoglobin production or quantitative impairment of hemoglobin production or both, and a disorder of red blood cell metabolism. Each possibility represents a separate embodiment of the invention.

In some embodiments, a red blood cell membrane disorder is selected from the group consisting of hereditary spherocytosis, hereditary elliptocytosis and paroxysmal nocturnal hemoglobinuria. Each possibility represents a separate embodiment of the invention.

In some embodiments, the blood disorder is a hemoglobinopathy.

In some embodiments, the hemoglobinopathy is thalassemia.

In some embodiments, the thalassemia type is selected from the group consisting of α-thalassemia and β-thalassemia. Each possibility represents a separate embodiment of the present invention. In some embodiments, the thalassemia type is selected from the group consisting of β-thalassemia minor, β-thalassemia intermedia and β-thalassemia major. Each possibility represents a separate embodiment of the present invention. In alternative or additional embodiments, the thalassemia type is selected from the group consisting of a silent carrier state α-thalassemia, α-thalassemia trait, hemoglobin H disease and α-thalassemia major. Each possibility represents a separate embodiment of the present invention.

In some embodiments, the hemoglobinopathy is a variant hemoglobin syndrome. In some embodiments, the syndrome is selected from the group consisting of a sickle-cell disease, HbC disease, HbE homozygosity (HbE disease) and HbE heterozygosity. Each possibility represents a separate embodiment of the invention.

In some embodiments, the syndrome is a sickle cells disease (also known as sickle cell anemia). Some sickle-cell diseases are associated with the HbS variant and include all manifestations of abnormal HbS levels, e.g. a homozygous sickle-cell disease (HbSS) and a mixed heterozygous hemoglobinopathy, also known as HbS heterozygosity (HbS/β-thalassemia, HbSC disease, and other combinations). In some embodiments, the sickle cell disease is selected from the group consisting of a homozygous sickle-cell disease (HbSS) and a mixed heterozygous hemoglobinopathy. Each possibility represents a separate embodiment of the invention.

In some embodiments, the syndrome is an HbC disease, also known as HbC homozygosity, which is associated with the HbC variant.

In some embodiments, the syndrome is selected from the group consisting of an HbE homozygosity and heterozygosity, which are associated with the HbE variant. Each possibility represents a separate embodiment of the invention.

In some embodiments, the disorder is a disorder of red blood cell metabolism. In some embodiments, the disorder is glucose-6-phosphate dehydrogenase (G6PD) deficiency.

In some embodiments, a disorder extrinsic to red blood cells results from an immunologic abnormality, an infection or a toxic substance. In some embodiments, the disorder extrinsic to red blood cells is selected from the group consisting of autoimmune hemolytic anemia and hemolytic uremic syndrome. Each possibility represents a separate embodiment of the invention.

In some embodiments, the disorder is hemolytic uremic syndrome.

In some embodiments, the blood disorder is idiopathic thrombocytopenic purpura.

In some embodiments, the disorder is lysis of red blood cells.

In some embodiments, the disorder is low levels of GSH in red blood cells.

In some embodiments, the disorder is poisoning caused by a toxic substance.

In some embodiments, the blood disorder is characterized by the appearance of Howell-Jolly bodies.

In some embodiments, the blood disorder is characterized by or resulting from asplenia or hyposplenism.

In some embodiments, the disorder is selected from the group consisting of a hemoglobinopathy, HUS, G6PD deficiency, lysis of red blood cells, and low levels of GSH in red blood cells.

In some embodiments, N-acetylcysteine (NAC) is administered together with the at least one peptide or salt thereof. In some embodiments, NAC and the peptide or salt thereof are within a single composition. According to these embodiments, the administered composition further comprises NAC. In other embodiments, NAC and the peptide or salt thereof are within separate compositions. In some embodiments, NAC and the peptide or salt thereof are administered sequentially. In other embodiments, NAC and the peptide or salt thereof are administered concurrently.

According to another aspect, the present invention provides a method for preserving a biological sample, the method comprising contacting said biological sample with a composition comprising at least one peptide having an amino acid sequence selected from the group consisting of:

Cys-Lys-Met-Cys; (SEQ ID NO: 1)

Cys-Met-Lys-Cys; (SEQ ID NO: 2)
and

Cys-β-Ala-His-Cys. (SEQ ID NO: 3)

According to yet another aspcet, the present invention provides a composition comprising at least one peptide or a salt thereof having an amino acid sequence selected from the group consisting of:

Cys-Lys-Met-Cys; (SEQ ID NO: 1)

Cys-Met-Lys-Cys; (SEQ ID NO: 2)
and

Cys-β-Ala-His-Cys, (SEQ ID NO: 3)

for use in the preservation of a biological sample.

In some embodiments, the preservation includes hypothermic preservation at temperatures below the physiological temperature but above freezing.

In some embodiments, the biological sample comprises cells selected from the group consisting of somatic cells, germ cells, gametes, and stem and progenitor cells. Each possibility represents a separate embodiment of the invention.

In some embodiments, the biological sample is a blood product.

In some embodiments, the blood product is selected from the group consisting of whole blood, plasma, red blood cells, white blood cells and platelets. Each possibility represents a separate embodiment of the invention.

Advantageously, preserving blood products according to the present invention permits storage of blood products for extended periods of time, while reducing or even preventing storage lesions and increasing survival and/or lifespan of blood cells following transfusion to a recipient.

In some embodiments, the peptide is not removed from the composition before transfusion to a recipient. In some embodiments, when the blood product is needed, the additive composition containing the blood product is directly infused into a recipient, without post-storage processing. In other embodiments, the peptide and optionally other components of the additive composition is removed from the composition before transfusion to a recipient. The composition may be subjected to further post-storage processing.

In some embodiments, the peptide present in the compositions of the present invention further comprises at least one modification of the peptide's terminus According to some embodiments, the peptide comprises an amino-terminal modification. According to other embodiments, the peptide comprises a carboxy-terminal modification. According to yet other embodiments, the peptide comprises both amino-terminal and carboxy-terminal modifications. Each possibility represents a separate embodiment of the invention.

In principle, any pharmaceutically acceptable group suitable for amino terminus modification, and any pharmaceutically acceptable group suitable for carboxy terminus modification may be used for the peptide used according to embodiments of the present invention.

In some embodiments, the amino terminal modification is an amino terminal blocking group.

In some typical embodiments, the amino-terminal blocking group is selected from the group consisting of alkyl and acyl. Each possibility represents a separate embodiment of the invention.

In some exemplary embodiments, the amino-terminal blocking group is an acetyl group.

In some embodiments, the amino terminal modification is a cell penetration-enhancing moiety, which improves the ability of the peptide to penetrate lipid layers and/or improves the ability of the peptide to penetrate into the skin. In some exemplary embodiments, the moiety that improves that ability of the peptide to penetrate lipid layers and/or improves its ability to penetrate the skin is a fatty acid. In some embodiments, the fatty acid is selected from the group consisting of palmitic acid, phosphatidic acid, stearic acid, arachidonic acid, docosahexaenoic acid, eicosapentaenoic acid, and oleic acid. Each possibility represents a separate embodiment of the invention.

In some embodiments, the amino terminal modification is selected from the group consisting of an amino terminal blocking group and a fatty acid. Each possibility represents a separate embodiment of the invention.

In some embodiments, the amino terminal modification is selected from the group consisting of alkyl, acyl and a fatty acid.

In some embodiments, the carboxy terminal modification is a carboxy terminal blocking group. In some typical embodiments, the carboxy terminal blocking group is selected from the group consisting of amide, ester and alcohol group. Each possibility represents a separate embodiment of the invention. In some exemplary embodiments, the carboxy terminal blocking group is an amide group.

In some embodiments, the peptide is cleavable by intracellular peptidases.

In some additional or alternative embodiments, the N- and/or C-terminal modifications are hydrolysable by intracellular enzymes. Thus, these modifications may be hydrolyzed upon entry of the peptide into cells.

In some embodiments, the middle dipeptide, located between the two Cys residues, is selected from the group consisting of Lys-Met and Met-Lys. Each possibility represents a separate embodiment of the invention. Lysine and methionine are precursors for the biosynthesis of carnitine molecules. In living cells, carnitine is required for the transport of fatty acids from the cytosol into the mitochondria where the breakdown of lipids takes place during the generation of metabolic energy. Carnitine is also known to have strong antioxidant activity. As noted above, the peptide may be cleaved by peptidases upon entry into cells. In some embodiments, the peptide undergoes cleavage that results in the release of lysine and methionine.

In some embodiments, the dipeptide β-Ala-His is located between the two Cys residues. The dipeptide β-Ala-His (β-alanyl-L-histidine) is known as carnosine. Carnosine is capable of performing a variety of functions, including anti-oxidation, anti-glycation, pH buffering and chelation of divalent metal cations. In some embodiments, the peptide undergoes intracellular cleavage that results in the release of free carnosine.

In some specific exemplary embodiments, the composition comprises the peptide N-acetyl-Cys-Lys-Met-Cys-amide (SEQ ID NO: 4).

In additional specific exemplary embodiments, the composition comprises the peptide N-acetyl-Cys-Met-Lys-Cys-amide (SEQ ID NO: 5).

In yet additional specific exemplary embodiments, the composition comprises the peptide N-acetyl-Cys-β-Ala-His-Cys-amide (SEQ ID NO: 6).

In some embodiments, the peptide is in the form of a salt. In some embodiments, the salt is selected from the group consisting of trifluoroacetic acid (TFA), acetate and citrate salts. Each possibility represents a separate embodiment of the invention.

According to another aspect, the present invention provides at least one peptide or a salt thereof having an amino acid sequence selected from the group consisting of:

Cys-Lys-Met-Cys, (SEQ ID NO: 1)

Cys-Met-Lys-Cys; (SEQ ID NO: 2)
and

Cys-β-Ala-His-Cys, (SEQ ID NO: 3)

for use in the treatment of a blood disorder associated with glutathione dysregulation.

According to yet another aspect, the present invention provides the use of at least one peptide or a salt thereof having an amino acid sequence selected from the group consisting of:

Cys-Lys-Met-Cys, (SEQ ID NO: 1)

Cys-Met-Lys-Cys; (SEQ ID NO: 2)
and

Cys-β-Ala-His-Cys, (SEQ ID NO: 3)

in the manufacture of a medicament for treating a blood disorder associated with glutathione dysregulation.

These and further aspects and features of the present invention will become apparent from the detailed description, examples and claims which follow.

DETAILED DESCRIPTION OF THE INVENTION

Figure 1A:
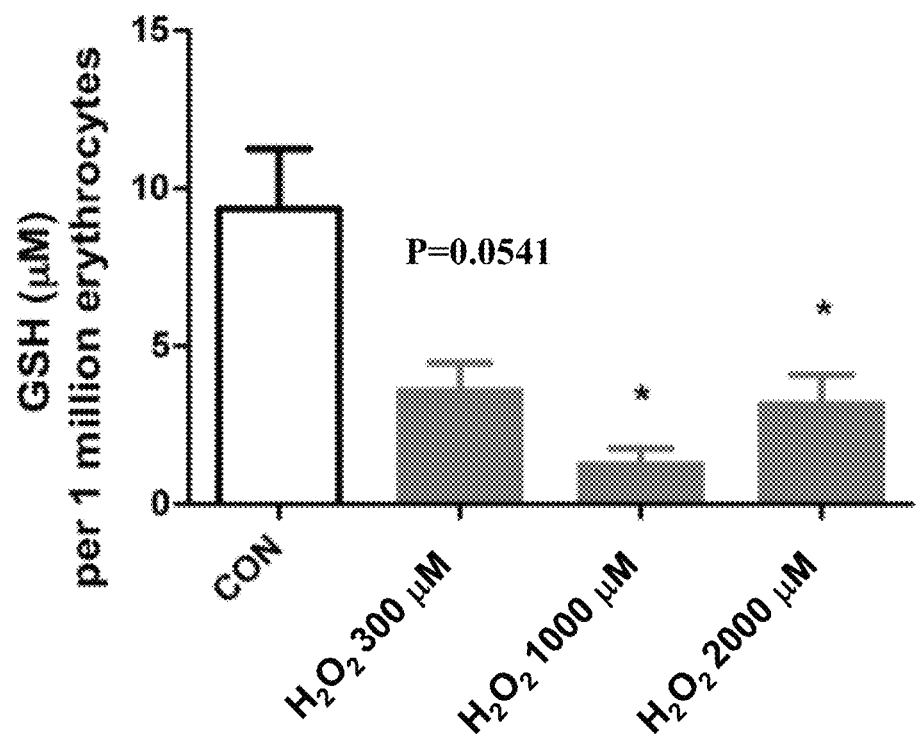
FIGS. 1A-1D. Effects of peptides according to embodiments of the present invention on glutathione status in murine erythrocytes subjected to oxidative stress.

The present invention relates to the use of thiol-containing peptides as therapeutic agents in the treatment of blood disorders characterized by glutathione dysregulation and in the treatment of blood disorders characterized by alterations in GSH:GSSG normal ratio within the blood cells. The present invention further relates to the use of thiol-containing peptides as protective agents in preservation of biological material.

DEFINITIONS

As used herein, the term "glutathione dysregulation" refers to an altered, imbalanced, intra-cellular or extra-cellular GSH:GSSG ratio (reduced to oxidized glutathione levels) compared to a desired ratio, that is considered normal, as known in the art. The term also encompasses shortage of reduced glutathione. Glutathione (gamma-glutamyl-cysteinyl-glycine) is a sulfhydryl (—SH) antioxidant, antitoxin and enzyme co-factor. Being water-soluble, it is found mainly in the cell cytosol and other aqueous phases of living systems. Glutathione exists in two forms-reduced (GSH) and oxidized (GSSG), the latter is a sulfur-sulfur (S—S) linked compound containing two glutathione molecules. The sulfur-sulfur linkage is reversible upon re-reduction. GSH is under tight homeostatic control both intracellularly and extracellularly. A dynamic balance is maintained between GSH synthesis, recycling from GSSG/oxidized glutathione, and utilization. A balance between GSH and GSSG is a major mechanism by which cells and tissues maintain a stable redox state. When cells or tissues are exposed to an increased level of oxidative stress, GSSG accumulates and the ratio of GSH to GSSG decreases. The determination of the GSH:GSSG ratio and the quantification of GSH and/or GSSG are useful indicators of oxidative stress in cells and tissues.

As used herein, the term "blood disorder" refers to a disease or disorder in which at least one type of blood cells and/or other blood components, including red blood cells, white blood cells and platelets, are affected, leading to impaired functioning of the at least one type of blood cells and/or other blood components.

As used herein, the term "blood disorder associated with glutathione dysregulation" refers to a blood disorder with clinical manifestations that are caused and/or influenced by glutathione dysregulation, and/or characterized by decreased levels or concentrations of reduced gluthatione in blood cells or plasma. The term typically refers to diseases or disorders characterized by oxidative damage of blood cells, and/or an abnormal GSH levels within blood cells, particularly red blood cells. The term also encompasses blood disorders where viability and functioning of blood cells can be improved by elevating reduced glutathione levels even above normal level.

As used herein, "treating" and "treatment", refers to reduction, amelioration or even elimination of at least some of the symptoms associated with the relevant disease. For example, the term may include anemia reduction. The term may include hemolysis reduction. The term may include increasing the levels of reduced glutathione within different types of blood cells, e.g. red blood cells, white blood cells and platelets, and/or prolongation of red blood cell survival. The term may include preventing a decrease in the level of reduced glutathione within the cells. The term may also include protection of platelets and white blood cells (including but not limited to polymorphonuclear cells). The term may further include improvement of additional clinical manifestations, including but not limited to, reduction of thromboembolic complications, kidney function improvement and spleen size reduction.

The term "treatment" may also encompass prophylactic treatment, which may be applied to populations at risk of developing the diseases or disorders described herein. For example, individuals known to carry a certain mutation that is associated with a particular disease.

As used herein, the terms "reducing" or "decreasing" when referring to a level of a certain substance or to a measureable index, are intended to refer to reduction compared to an initial level, prior to treatment as described herein.

As used herein, the term "biological sample" encompases blood products, all kinds of cells, tissues, organs, and organisms, all of which can be natural or genetically or otherwise modified. The organisms include animals, plants, fungus, micro-organisms, and viruses. The cells include prokaryotic and eukaryotic cells. The term also encompasses embryos, such as human embryos and embryos of other organisms, including mammals.

As used herein, the term "blood product" refers to a preparation containing whole blood or one or more separated blood componemts. The blood components may be selected from the group consisting of plasma, red blood cells, white blood cells and platelets.

As used herein, the terms "preserving" and "preservation", when referring to a biological sample, indicate storing such that sustained viability and/or quality of the biological sample is supported or maintained. The biological activity of the sample is sometimes considerably reduced in the preservation state, and may be resumed when taken out of the preservation state.

As used herein "peptide" indicates a sequence of amino acids linked by peptide bonds. In some embodiments, a peptide is composed of 10 amino acids or less, 9 amino acids or less, 8 amino acids or less, 7 amino acids or less, 6 amino acids or less, 5 amino acids or less, or 4 amino acids. Each possibility represents a separate embodiment of the invention. In some embodiments, the peptide is composed of 4-10 amino acids, 4-9 amino acids, 4-8 amino acids, 4-7 amino acids, 4-6 amino acids, 4-5 amino acids, or 4 amino acids. Each possibility represents a separate embodiment of the invention. In some embodiments, a tetra-peptide is provided. The term "tetra-peptide" indicates a peptide composed of four amino acids. The peptides of the present invention are typically utilized in a linear form, although it will be appreciated that in cases where cyclization does not severely interfere with peptide characteristics, cyclic forms of the peptide can also be utilized.

The term "amino acid" refers to compounds, which have an amino group and a carboxylic acid group, preferably in a 1,2- 1,3-, or 1,4-substitution pattern on a carbon backbone. The term encompasses natural, non-natural and/or chemically modified amino acid residues. Natural amino acids include those found in proteins, which are L-amino acids. Non-natural and/or chemically modified amino acids include, for example, the corresponding N-methyl amino acids, side chain modified amino acids and the biosynthetically available amino acids which are not found in proteins (e.g., 5-hydroxy-lysine). The amino acid residues are represented throughout the specification and claims by either one or three-letter codes, as is commonly known in the art. The amino acids used in this invention are those which are available commercially or are available by routine synthetic methods. Certain residues may require special methods for incorporation into the peptide, and either sequential, divergent or convergent synthetic approaches to the peptide sequence are useful in this invention.

Also included within the scope of the invention are salts of the peptides, and derivatives of the peptides of the invention.

As used herein the term "salts" refers to salts of carboxyl groups and to acid addition salts of amino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, acetic acid or oxalic acid. Additional examples of suitable salts include trifluoroacetic acid (TFA), acetate and citrate salts.

Esters and amides of carboxy groups and acyl and alkyl derivatives of amino groups may be introduced into the molecule by reacting targeted amino acid residues of the peptide with an organic derivatizing agent that is capable of reacting with terminal residues. Preferred chemical derivatives include peptides that have been C-termini amidated or N-termini acetylated.

"Derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups).

"Permeability" refers to the ability of an agent or substance to penetrate, pervade, or diffuse through a barrier, membrane, or a skin layer. A "cell permeability-enhancing", "cell penetration-enhancing" or "permeability-enhancing" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds. The permeability-enhancing moiety may be connected to any position in the peptide moiety, directly or through a spacer, preferably to the amino or carboxy terminus of the peptide moiety.

As used herein, the term "about", when referring to a measurable value such as an amount or size, is meant to encompass variations of +/−10%, more preferably +/−5%, even more preferably +1-1%, and still more preferably +/−0.1% from the specified value, as such variations are appropriate to achieve the intended purpose.

Peptides

The present invention utilizes peptides and/or salts thereof having an amino acid sequence selected from the group consisting of:

```
                             (SEQ ID NO: 1)
Cys-Lys-Met-Cys, (SEQ ID NO: 2)
Cys-Met-Lys-Cys, (SEQ ID NO: 3)
Cys-beta-Ala-His-Cys,
```

Each possibility represents a separate embodiment of the invention.

It is understood that Cys represents the amino-acid cysteine; Lys represents the amino-acid lysine; Met represents the amino-acid methionine; and β-Ala represents the amino-acid β-alanine.

It is now disclosed for the first time that these peptides are capable of elevating GSH levels and/or balancing the GSH: GSSG ratio in favor of reduced glutathione, and alleviating oxidative stress within cells. These peptides can be used for preserving viability and functioning of blood, blood components, cells and organs more effectively than previously achieved with known peptides or compounds such as N-acetylcysteine amide.

In some embodiments, the peptide further comprises at least one modification selected from the group consisting of an amino-terminal modification and a carboxy-terminal modification. According to these embodiments, the peptide is selected from the group consisting of:

```
                             (SEQ ID NO: 7)
Z-Cys-Lys-Met-Cys-Y, (SEQ ID NO: 8)
Z-Cys-Met-Lys-Cys-Y;
and (SEQ ID NO: 9)
Z-Cys-β-Ala-His-Cys-Y,
``` wherein Z is absent or represents an amino terminal modification and Y is absent or represents a carboxy terminal modification.

In some embodiments, the N- and C-termini modifications reduce the polarity of the peptides of the present invention, thus facilitating the ability of these peptides to cross cell membranes, enter easily into cells and accumulate within the cells. In addition, modifications of the peptide termini may improve bio-stability, for example by blocking the action of peptidases.

The amino and carboxy termini modifications may be chosen from any amino and carboxy termini modifications conventionally used in the art of peptide chemistry, which will not adversely affect the activities of the peptide.

In some embodiments, the amino terminal modification comprises addition of an amino terminal blocking group.

Blocking of the N terminus may be performed, for example, by alkylation or acylation, using methods well known in the art. Non-limiting examples of suitable N-terminal blocking groups include $C_1$-$C_5$ branched or unbranched alkyl groups, acyl groups such as formyl and acetyl groups, and substituted forms thereof, such as the acetamidomethyl (Acm) group. Each possibility represents a separate embodiment of the invention.

In some embodiments, the amino terminal modification comprises covalently linking to the N-terminus of the peptide a moiety that improves the ability of the peptide to penetrate lipid layers and/or improves the ability of the peptide to penetrate into the skin. Such moiety may provide high efficacy topical administration. In some exemplary embodiments, the moiety is a fatty acid. The fatty acid may be selected from the group consisting of palmitic acid, phosphatidic acid, stearic acid, arachidonic acid, docosahexaenoic acid, eicosapentaenoic acid and oleic acid. Each possibility represents a separate embodiment of the invention.

In some typical embodiments, the amino terminal modification is selected from the group consisting of acetyl, alkyl, acyl and a fatty acid. Each possibility represents a separate embodiment of the invention.

In some embodiments, the carboxy terminal modification is a carboxy terminal blocking group.

Blocking of the C terminus may be performed, for example, by amidation, reduction or esterification, using methods well known in the art. Non-limiting examples of suitable C-terminal blocking groups include amide, ester, and alcohol groups. Each possibility represents a separate embodiment of the invention.

Upon entry of the peptides into cells they may undergo cleavage by intracellular peptidases.

In addition, the N- and/or C-termini modifications of the peptides may be hydrolyzed, which may result in their accumulation in the cytosol.

In some embodiments, the peptide is a tetra-peptide selected from the group consisting of: Cys-Lys-Met-Cys (SEQ ID NO: 1), Cys-Met-Lys-Cys (SEQ ID NO: 2); and Cys-β-Ala-His-Cys (SEQ ID NO: 3).

In some embodiments the middle dipeptide, located between the two Cys residues, is selected from the group consisting of Lys-Met and Met-Lys. In some embodiments, a peptide is provided, selected from the group consisting of Cys-Lys-Met-Cys (SEQ ID NO: 1) and Cys-Met-Lys-Cys (SEQ ID NO: 2).

In some exemplary embodiments, the peptide N-acetyl-Cys-Lys-Met-Cys-amide (SEQ ID NO: 4) is provided.

In additional exemplary embodiments, the peptide N-acetyl-Cys-Met-Lys-Cys-amide (SEQ ID NO: 5) is provided.

In some embodiments the dipeptide β-Ala-His, is located between the two Cys residues. In some embodiments, a peptide Cys-β-Ala-His-Cys (SEQ ID NO: 3) is provided. In some exemplary embodiments, the peptide N-acetyl-Cys-β-Ala-His-Cys-amide (SEQ ID NO: 6) is provided.

The peptides may be synthesized by any technique known to those skilled in the art of peptide synthesis. These methods include solid phase as well as solution phase synthesis methods.

Solid phase peptide synthesis procedures are well known in the art and further described by John Morrow Stewart and Janis Dillaha Young, Solid Phase Peptide Syntheses (2nd Ed., Pierce Chemical Company, 1984).

A skilled artesian may synthesize any of the peptides of the present invention by using an automated peptide synthesizer using standard chemistry such as, for example, t-Boc or Fmoc chemistry.

The methods include exclusive solid phase synthesis, partial solid phase synthesis methods, fragment condensation, classical solution synthesis.

Synthetic peptides can be purified by preparative high performance liquid chromatography (Creighton T. (1983) Proteins, structures and molecular principles. WH Freeman and Co. N.Y.) and the composition of which can be confirmed via amino acid sequencing. Some of the peptides of the invention, which include only natural amino acids, may further be prepared using recombinant DNA techniques known in the art. The conjugation of the peptidic and permeability moieties may be performed using any methods known in the art, either by solid phase or solution phase chemistry. Some of the compounds of the present invention may conveniently be prepared using solution phase synthesis methods. Other methods known in the art to prepare compounds like those of the present invention can be used and are comprised in the scope of the present invention.

The permeability-enhancing moiety of the present invention may be connected to any position in the peptide moiety, directly or through a spacer. According to a specific embodiment, the cell-permeability moiety is connected to the amino terminus of the peptide moiety. The optional connective spacer may be of varied lengths and conformations comprising any suitable chemistry including but not limited to amine, amide, carbamate, thioether, oxyether, sulfonamide bond and the like. Non-limiting examples for such spacers include amino acids, sulfone amide derivatives, amino thiol derivatives and amino alcohol derivatives.

Cyclic versions of the peptides disclosed herein are also within the scope of the present invention. Cyclization of peptides may take place by any means known in the art, for example through free amino and carboxylic groups present in the peptide sequence, or through amino acids or moieties added for cyclization. Non limiting examples of cyclization types are: side chain to side chain cyclization (e.g., through S—S bonds), C-to-N terminal cyclization, side chain to terminal cyclization, and any type of backbone cyclization incorporating at least one N-ω-substituted amino acid residue/s as described for example in WO 95/33765.

Other methods known in the art to prepare peptides like those of the present invention can be used and are within the scope of the present invention.

In some embodiments, the peptide is in the form of a salt. Non-limiting examples of suitable salts include trifluoroacetic acid (TFA), acetate and citrate salts.

Compositions of the Present Invention

According to an aspect of the present invention, there is provided a pharmaceutical composition comprising as an active ingredient at least one peptide or a salt thereof having an amino acid sequence selected from the group consisting of:

```
                                        (SEQ ID NO: 1)
         Cys-Lys-Met-Cys, (SEQ ID NO: 2)
         Cys-Met-Lys-Cys;
         and (SEQ ID NO: 3)
         Cys-β-Ala-His-Cys,
``` for use in the treatment of a blood disorder associated with glutathione dysregulation.

The compositions and methods of the present invention are typically employed for the treatment of a mammal, preferably a human.

In some embodiments, the composition comprises N-acetylcysteine (NAC). NAC may be identified by CAS Registry Number 616-91-1. NAC is commercially available and may also be synthesized by methods known in the art.

In some typical embodiments, the composition further comprises a pharmaceutically acceptable diluent, excipient or carrier.

As used herein, the term "pharmaceutically acceptable diluent, excipient, or carrier" refers to a diluent, excipient, or carrier that does not cause significant irritation to an organism and does not abrogate the biological activity and properties of the administered active agent.

As used herein, the term "excipient" refers to an inert substance added to a pharmaceutical composition to further facilitate administration of an active ingredient. Non-limiting examples of excipients include calcium carbonate, calcium phosphate, various sugars and types of starch, cellulose derivatives, gelatin, vegetable oils, and polyethylene glycols. Techniques for formulation and administration of drugs may be found in "Remington's Pharmaceutical Sciences", Mack Publishing Co., Easton, Pa., (Remington: The Science and Practice of Pharmacy, Gennaro, A., Lippincott, Williams & Wilkins, Philadelphia, Pa., 20th ed, 2000).

In some embodiments, a therapeutic composition comprises a pharmaceutically acceptable carrier. As used herein, a "carrier" refers to any substance suitable as a vehicle for delivering of the agents or molecule of the present invention to a suitable in vivo or in vitro site. As such, carriers can act as a pharmaceutically acceptable excipient of a therapeutic composition of the present invention. Carriers of the present invention include: (1) excipients or formularies that transport, but do not specifically target a molecule to a cell (referred to herein as non-targeting carriers); and (2) excipients or formularies that deliver a molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Therapeutic compositions of the present invention can be sterilized by conventional methods.

In some embodiments, the composition further comprises at least one more active ingredient.

In some embodiments, a pharmaceutical composition is provided, consisting of the peptide of the present invention as an active ingredient.

The peptide of the present invention or a salt thereof, and optionally additional one or more active ingredients, are present in the compositions of the present invention in an amount effective to achieve the intended purpose, for example, in an amount effective to treat a certain disease.

Any suitable route of administration may be used for the composition of the present invention, including but not limited to local and systemic routes. Systemic administration includes all enteral and all parenteral routes. Non-limiting examples of suitable administration routes include topical application, oral, rectal, transmucosal such as transnasal and buccal, intravenous, intramuscular, transdermal, subcutaneous, intradermal, intravitreal, intravesicular and inhalation routes. Each possibility represents a separate embodiment of the invention. The compositions of the present invention may be formulated for sustained release of the active ingredient.

Thus, in some embodiments, the composition of the present invention is formulated for topical administration. In other embodiments, the composition is formulated for systemic administration.

Pharmaceutical compositions of the present invention may be formulated in conventional manners. The proper formulation is dependent upon the route of administration chosen.

In some embodiments, the compositions of the present invention are formulated for topical use. Non-limiting examples of formulations for topical use include cream, ointment, lotion, gel, foam, suspension, aqueous or cosolvent solutions, salve, liposome and sprayable liquid form. The composition may also form part of a patch for transdermal application. Other suitable topical product forms for the compositions of the present invention include, for example, emulsion, mousse, lip balm, lip gloss, lotion, mask, pomade, solution and serum.

In some embodiments, the pharmaceutical compositions are formulated in the form of a solid or soft gel, for example, an aqueous-alcoholic gel and a clear gel. Typically, the aqueous phase comprises one or more gelling agents, for example cellulose gelling agents, or synthetic gelling agents.

In some embodiments, the compositions of the present invention are formulated for oral administration. For oral administration, enteric-coated preparations or dosage forms, microspheres, liposomes and nanoparticles for oral delivery of peptides and proteins may be used. Non-limiting examples of formulations for oral administration include tablets, pills, dragees, capsules, liquids, gels, syrups, slurries, suspensions, and the like, for oral ingestion by a patient. Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

For administration by injection, the active ingredients of the composition may be formulated in aqueous solutions, for example in physiologically compatible buffers including but not limited to Hank's solution, Ringer's solution, or physiological salt buffer. Formulations for injection may be presented in unit dosage forms, for example, in ampoules, or in multi-dose containers with, optionally, an added preservative. The compositions may be in the form of suspensions, solutions, or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, for example, a sterile, pyrogen-free, water-based solution, before use.

For transmucosal administration, penetrants appropriate to the barrier to be permeated are used in the formulation. Such penetrants are generally known in the art.

For buccal administration, the compositions may take the form of tablets or lozenges formulated in conventional manner.

For administration by inhalation route, the active ingredients are conveniently delivered in the form of an aerosol spray presentation from a pressurized pack or a nebulizer with the use of a suitable propellant, for example, dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

In some embodiments, the compositions of the present invention are formulated for rectal administration, for example, as suppositories or retention enemas, using, for example, conventional suppository bases such as cocoa butter or other glycerides.

The exact formulation, route of administration, and dosage can be chosen by the individual physician in view of the patient's condition.

In some embodiments, the composition further comprises at least one additive useful in the pharmaceutical fields, including, but not limited to fats, emulsifiers and co-emulsifiers, hydrophilic or lipophilic gelling agents, colorants, fragrances, emollients, humectants, preservatives, vitamins, chelators, solvents, fillers, thickeners, hydrophilic and lipophilic filters, dyestuffs, neutralizers, penetration-enhancing agents and polymers.

Non-limiting examples of suitable fats include mineral oils, oils of animal origin (lanolin), synthetic oils (isopropyl myristate, octyldodecyl, isostearyl isostearate, decyl oleate or isopropyl palmitate), silicone oils (cyclomethicone or dimethicone) and fluorinated oils. Fatty alcohol, fatty acids, waxes and gums, notably silicone gums and elastomers can also be used as fats.

Non-limiting examples of suitable emulsifiers and co-emulsifiers include polyglycerol fatty acid esters, sucrose fatty acid esters, sorbitane fatty acid esters, oxyethylene sorbitan fatty acid esters, PEG fatty alcohol ethers, glycerol fatty acid esters, alkyl sulphates, alkyl ether sulphates, alkyl phosphates, alkyl polyglucosides and dimethicone copolyols.

Non-limiting examples of suitable hydrophilic gelling include carboxyvinyl polymers (carbomer), acrylic copolymers such as acrylate/alkylacrylate copolymers, polyacrylamids, polysaccharides such as xanthan gum, guar gum, natural gums such as cellulose gum and derivatives, clays and 2-acrylamido-2-methylpropane acid copolymers.

Non-limiting examples of suitable lipophilic gelling agents include modified clays such as bentones, fatty acid metal salts, hydrophobic silica and ethylcellulose.

Non-limiting examples of suitable fillers include talc, kaolin, mica, serecite, magnesium carbonate, aluminum silicate and organic powders such as nylon.

Non-limiting examples of suitable dyestuffs include lipophilic dyes, hydrophilic dyes, pigments and mother-of-pearl commonly used in dermatological compositions, and their mixtures.

Non-limiting examples of suitable neutralizers include soda, triethanolamine, aminomethyl propanol and potassium hydroxide.

Non-limiting examples of suitable penetration enhancing agents include alcohols and glycols (ethanol and propylene glycol), ethoxydiglycol, alcohols and fatty acids (oleic acid), fatty acid esters and dimethyl isosorbide.

Non-limiting examples of preservatives compatible with pharmaceutical compositions include benzoic acid, its salts and esters, sorbic acid and its salts, parabens and their salts, triclosan, imidazolidinyl urea, phenoxyethanol, DMDM hydantoin, diazolidinyl urea and chlorphenesin.

Conventionally, the filters are UVA and UVB filters. Non-limiting examples of suitable UVA and UVB filters include organic filters such as benzophenone-3, butyl methoxydibenzoyl methane, octocrylene, octyl methoxycinnamate, 4-methylbenzylidene camphor, octyl salicylate, terephthalylidene dicamphor sulfonic acid and drometrizole trisiloxane, and non-organic filters such as titanium oxide and zinc oxide.

Non-limiting examples of suitable solvents include water, ethanol, glycerin, propylene glycol, butylene glycol and sorbitol.

The quantities and concentrations of these various additives are those conventionally used in pharmaceutical preparations as is known to a person skilled in the art.

According to another aspect of the present invention, there is provided a composition comprising at least one peptide or a salt thereof having an amino acid sequence selected from the group consisting of:

Cys-Lys-Met-Cys, (SEQ ID NO: 1)

Cys-Met-Lys-Cys; (SEQ ID NO: 2)
and

Cys-β-Ala-His-Cys, (SEQ ID NO: 3)

for use in the preservation of a biological sample.

The composition may further include additional standard additives known in the art for storing relevant biological samples.

For example, standard additive-compositions for storing red blood cells include, but are not limited to, compositions containing anticoagulants, adenine-glucose-saline, compositions containing adenine-glucose-saline-mannitol, and compositions ontaining adenine-glucose-saline-citrate-phosphate-dextrose (see, e.g., Hess, J. R., 2006 Vox Sanguinis 91:13-19; U.S. Pat. Nos. 6,770,478, 6,527,957, 6,267,925, 5,789,151, 5,250,303, 5,248,506, 5,147,776, 4,812,310, 4,585,735).

Standard additive-compositions for platelets include, for example, carbohydrates such as glucose, sucrose, or mannitol, or other compatible carbohydrates.

Other additives such as glycerol, anticoagulants, antibiotics and/or other materials for preventing contamination may also be added to the mixture.

Information regarding additives and other components that may be added to a composition intended for preserving blood and blood products can be found, for example, in "Guide to preparation, use and quality assurance of blood components" 16th. Edition, by European Directorate for the Quality of Medicines & HealthCare, Council of Europe.

Methods and Uses of the Present Invention

According to one aspect of the present invention, there is provided herein a method for treating a blood disorder associated with glutathione dysregulation in a subject in need thereof, the method comprising administering to the subject a pharmaceutical composition comprising as an active ingredient at least one peptide having an amino acid sequence selected from the group consisting of:

Cys-Lys-Met-Cys, (SEQ ID NO: 1)

Cys-Met-Lys-Cys; (SEQ ID NO: 2)
and

Cys-β-Ala-His-Cys, (SEQ ID NO: 3)

for treating the blood disorder in the subject.

In some embodiments, the disorders involve or are characterized by hemolytic anemia, with premature destruction of red blood cells. Hemolytic anemia is a form of anemia due to an abnormal breakdown of red blood cells, either in the blood vessels (intravascular hemolysis) or elsewhere in the human body (extravascular).

In some embodiments, the blood disorder is an intrinsic abnormality of blood cells, such as intrinsic abnormality of red blood cells (RBC).

An intrinsic abnormality of red blood cells refers to defects intrinsic to red blood cells, such as defects in one or more components or functions, including the cell membrane, hemoglobin production and cell metabolism.

Hereditary and acquired red blood cell membrane disorders, characterized by defects and abnormalities of different components of the cell membrane, include, for example, hereditary spherocytosis, hereditary elliptocytosis and paroxysmal nocturnal hemoglobinuria.

Hereditary spherocytosis and hereditary elliptocytosis are both genetic diseases caused by alterations in the genes that code for RBC membrane proteins, including inter alia, spectrin (alpha and beta), ankyrin, band 3 protein, protein 4.1 and protein 4.2, which are necessary to maintain the normal shape of an erythrocyte. In hereditary spherocytosis, red blood cells are produced which are sphere-shaped rather than bi-concave disk shaped, and are more prone to hemolysis. In hereditary elliptocytosis, genetic mutations result in weakness of the cell cytoskeleton, leading to deformation of the cell. The RBCs of the patients are oval or elliptical. Symptoms of the two conditions include variable degrees of anemia, jaundice, and splenomegaly. Classification and gene defects of hereditary spherocytosis are reviewed, for example, in Bolton-Maggs et al. (2004) *British Journal of Haematology*, 126: 455-474. Classification and gene defects of hereditary elliptocytosis are reviewed, for example, in Gallagher (2004) *Seminars in Hematology*, 41(2): pp 142-164.

Paroxysmal nocturnal hemoglobinuria is caused by a membrane defect in hematopoietic stem cells and their progeny, including RBCs, WBCs, and platelets. The defect is a missing glycosyl-phosphatidyl-inositol anchor for membrane proteins, leading to ongoing intravascular hemolysis of RBCs, and diminished marrow production of WBCs and platelets.

Disorders of hemoglobin production, where hemoglobin production is impaired, are known as hemoglobinopathies. In some embodiments, the blood disorder is hemoglobinopathy. Hemoglobinopathy may be selected from a thalassemia, characterized by reduced synthesis of globin subunits that are structurally normal, and a structural hemoglobin variant syndrome, characterized by the synthesis of structurally abnormal globin subunits. Both types are caused by mutations and/or deletions in the globin related genes. Some hemoglobinopathies are mixed forms that combine features of the two main types. The different types of thalassemias and hemoglobin variants are reviewed, for example, in Kohne et al. (2011) *Dtsch Arztebl Int.* 108(31-32):532-40; and Batt and Reske (2010) The Hospital Physician® Board Review Manuals, Hematology, Volume 5, Part 3 pp1-12, Hemoglobinopathies, published by Turner White Communications, Inc., In some embodiments, the hemoglobinopathy is thalassemia.

In some embodiments, the thalassemia type is selected from the group consisting of alpha-thalassemia (resulting from a deletion or mutation in one or more of the four α-globin genes) and beta-thalassemia (resulting from a deletion or mutation in one or more of the two β-globin genes). Each possibility represents a separate embodiment of the invention. In some embodiments, the beta-thalassemia is selected from the group consisting of β-thalassemia minor, β-thalassemia intermedia and β-thalassemia major. Each possibility represents a separate embodiment of the invention. In some embodiments, the alpha-thalassemia is selected from the group consisting of a silent carrier state α-thalassemia, α-thalassemia trait, hemoglobin H disease and α-thalassemia major. Each possibility represents a separate embodiment of the invention.

In some embodiments, the hemoglobinopathy is a variant hemoglobin syndrome. In some embodiments, the syndrome is selected from the group consisting of a sickle-cell disease, HbC disease, HbE homozygosity (HbE disease) and HbE heterozygosity. Each possibility represents a separate embodiment of the invention.

Sickle cell diseases are associated with the HbS variant and include all manifestations of abnormal HbS levels, e.g. a homozygous sickle-cell disease (HbSS) and a mixed heterozygous hemoglobinopathy (HbS/β-thalassemia, HbSC disease, and other combinations). Each possibility represents a separate embodiment of the invention.

HbC disease, also known as HbC homozygosity, is associated with the HbC variant. HbE homozygosity and heterozygosity are associated with the HbE variant. Each possibility represents a separate embodiment of the invention.

In some embodiments, the syndrome is selected from the group consisting of a sickle-cell disease, HbS heterozygosity, sickle-cell β$^+$-thalassemia, sickle-cell β$^0$-thalassemia, HbSC disease, HbC disease, HbC heterozygosity, HbE heterozygosity, HbE disease, HbE β$^+$-thalassemia, HbE β$^0$-thalassemia, a hemoglobinopathy with unstable Hb, and abnormal hemoglobins with disruptions to O$_2$ transportation function. Each possibility represents a separate embodiment of the invention.

In some embodiments, the syndrome is sickle-cell disease (also known as sickle cell anemia).

Disorders of RBC cell metabolism include, for example G6PD deficiency. In some embodiments, the disorder is G6PD deficiency.

G6PD deficiency is an X-linked recessive hereditary disease characterized by abnormally low levels of the enzyme glucose-6-phosphate dehydrogenase. This enzyme is a metabolic enzyme involved in the pentose phosphate pathway, which is particularly important in red blood cell metabolism. G6PD also plays an important role in the production of reduced nicotinamide adenine dinucleotide phosphate (NADPH). NADPH is necessary for the regeneration of reduced glutathione through reducing oxidized glutathione (GSSG). G6PD deficient red blood cells are therefore highly vulnerable to oxidative stress and tend to hemolyze.

In some embodiments, the blood disorder is extrinsic to the RBCs.

Disorders extrinsic to the RBC may result, for example, from immunologic abnormalities (e.g. autoimmune hemolytic anemia), and certain infections and/or action of toxic substances (e.g. hemolytic uremic syndrome, lead poisoning).

Autoimmune hemolytic anemia (AIHA, also known as non-hereditary spherocytosis) is caused by auto-antibodies reactive against RBCs, leading to their lysis. The disease may be primary or secondary to another underlying illness. Primary AIHA is idiopathic. Secondary AIHA can result from other illnesses, such as lymphoproliferative disorders (e.g. chronic lymphocytic leukemia, lymphoma) and other autoimmune disorders (e.g. systemic lupus erythematosis, rheumatoid arthritis, scleroderma, ulcerative colitis). Secondary AIHA has also found to be associated with the use of certain medications. Classification of AIHA includes warm AIHA, cold agglutinin syndrome, paroxysmal cold hemoglobinuria, mixed-type AIHA, and drug-induced AIHA. Information may be found, for example, in Gehrs and Friedberg (2002) *Am J Hematol,* 69(4):258-71.

In some embodiments, the disorder is hemolytic uremic syndrome (HUS). HUS is a condition resulting from an abnormal premature destruction of red blood cells following a gastrointestinal infection caused by *Escherichia coli,* which produces toxic substances that destroy the cells. The condition has also been linked to other gastrointestinal infections, including *Shigella* and *Salmonella,* as well as non-gastrointestinal infections and other factors such as adverse drug reaction and drug overdose. The damaged red blood cells usually clog the filtering system in the kidneys, which may eventually cause a life-threatening kidney failure. Classification of the different origins of hemolytic uremic syndrome is reviewed, for example, in Banerjee S (2009) *Indian Pediatr,* 46(12):1075-84.

In some embodiments, the blood disorder is characterized by the appearance of Howell-Jolly bodies, which are histopathological findings of nuclear remnants (clusters of DNA) in circulating erythrocytes. During maturation in the bone marrow erythrocytes normally expel their nuclei, but in some cases a small portion of DNA remains. Absence of splenic function, either following splenectomy, or occasionally due to splenic atrophy, may result in the appearance in the peripheral blood of red cells containing Howell-Jolly bodies. Howell-Jolly bodies are also observed in cases of accelerated or abnormal erythropoiesis.

In some embodiments, the blood disorder is characterized by or resulting from asplenia or hyposplenism. Asplenia may include functional or acquired, following splenectomy or an underlying diseases that destroys the spleen.

In some embodiments, the disorder is lysis of red blood cells.

In some embodiments, the disorder is low levels of GSH in red blood cells.

In some embodiments, the disorder is poor functioning of red blood cells.

Although the above disorders typically affect red blood cells, other blood cells may also be affected. In some embodiments, the blood cells affected by the blood disorders that can be treated and/or prevented using the compositions and methods of the present invention include red blood cells, platelets and PMN neutrophils.

In some embodiments, the blood disorder directly affects platelets. In some embodiments, the blood disorder is idiopathic thrombocytopenic purpura (ITP), which is a condition characterized by an abnormally low platelet count (thrombocytopenia) of unknown cause (idiopathic). As most incidents of ITP appear to be related to the production of antibodies against platelets, immune thrombocytopenic purpura or immune thrombocytopenia are also used to describe this condition.

The method of the present invention may be combined with one or more known treatments of the above described blood disorders.

In some embodiments, the method of the present invention comprises co-administering NAC. NAC may be administered before or after the peptide of the present invention. NAC and the peptide may be administered using the same administration route. Alternatively, NAC and the peptide may be administered using two different administration routes.

In some embodiments, the NAC is substantially free of its oxidized form, di-n-acetylcysteine. It is preferred that the therapeutic agent, serially or co-administered, be in any form in which it is typically available and the composition could be prepared in a manner that substantially prevents oxidation of the NAC during preparation or storage. In some embodiments of the invention, the preparation and storage of the formulation is performed in such a way that the reduced form of NAC is the primary form administered to the patient. Maintaining NAC containing formulations in solid form may be used for this purpose. When in solution, NAC containing formulations are preferably stored in a dark bottle that is vacuum sealed. Storage in cool dark environments is also preferred. The determination of reduced and oxidized species present in a sample may be determined by various methods known in the art, for example with capillary electrophoresis, HPLC, etc., as described, for example, by Chassaing et al. (1999) *J Chromatogr B Biomed Sci Appl* 735(2):219-27.

According to another aspect of the present invention, there is provided herein, a method for preserving a biological sample, the method comprising contacting said biological sample with a composition comprising at least one peptide having an amino acid sequence selected from the group consisting of:

```
                                            (SEQ ID NO: 1)
            Cys-Lys-Met-Cys, (SEQ ID NO: 2)
            Cys-Met-Lys-Cys;
            and (SEQ ID NO: 3)
            Cys-β-Ala-His-Cys,
``` for preserving the biological sample.

The term "contacting" may include, for example, mixing the sample with a composition comprising the peptide, or immersing or soaking the sample in a composition comprising the peptide.

In some embodiments, there is provided herein a method for preserving a blood product comprising mixing the blood product with the above composition.

In some embodiments, the blood product is whole blood.

The blood products can be obtained by any method known in the art, for example by processing a whole blood donation, or by apheresis where only the needed component is taken from the donor, the remainder been returned to the donor.

In other embodiments, the blood product is a blood component selected from the group consisting of whole blood, plasma, red blood cells, white blood cells and platelets.

Examples of particular blood products include, but are not limited to, whole blood, whole blood leucocyte-depleted, packed red cells, red cells-buffy coat removed, red cells leucocyte-depleted, red cells-washed, platelets recovered single unit, platelets recovered-pooled, platelets recovered pooled leucocyte-depleted, granulocytes apheresis.

In some embodiments, preserving a blood product as disclosed herein provides an extended storage period compared with conventional methods and compositions. For example, for red blood cells, the storage period may be extended beyond 7 weeks. Advantageously, the method of the present invention permits prolonged storage period of blood products, while maintaining the quality of the sample and/or better maintaining the quality of the sample within the same storage period. For example, the method may promote lower percentage of hemolysis, lower percentage of deformed cells, higher percentage of cells remaining in the circulation of a recipient following transfusion, maintained flexibility of red blood cells, and/or reduced fragility of red blood.

In some embodiments, preservation of blood products according to the present invention, particularly red blood cells, results in higher percentage of viable blood cells remaining in the circulation of a recipient following transfusion. Percentage of viable blood cells in the circulation of a recipient, such as red blood cells, is defined as the percentage of the stored red cells remaining in circulation of a recipient for 24 hours after infusion. The mean percentage is about 85%.

Percentage of viable cells remaining in the circulation of a recipient following transfusion may be tested in an animal model, for example, in mice.

Assessment of cell survival following storage may include performing cell count and morphology evaluations by microscopic observation. Percentage of hemolysis may be determined by methods known in the art, for example, by quantifying free hemoglobin levels in the sample (outside the red blood cells).

The function and viability of the platelets can be assessed by methods known in the art, for example, with assays of membrane function in response to hypotonic conditions (hypotonic shock response—HSR) and shape change in response to an activator (extent of shape change—ESC).

In some embodiments, preservation of blood product according to the present invention, particularly red blood cells, results in lower percentage (%) of hemolysis and/or lower fragility during storage compared to storage without the composition of the present invention.

In some embodiments, the preservation method of the present invention improves upon standard additive compositions by providing additional agents to the additive compositions. The method is not limited to a particular type or kind of standard additive composition configured for storing blood products, or to a particular method of storing blood products. Thus, the method of the present invention is typically combined with standard preservation conditions, including for example suitable temperature, agitation (where relevant and needed) and keeping the stored sample from contact with oxygen.

The various blood products, their preparation and accepted standards are described, for example, in "Guide to preparation, use and quality assurance of blood components" 16$^{th}$ edition, as noted above.

The particular temperature for preservation is determined according to a particular type of biological sample to be preserved and a specific use, as known in the art.

In some embodiments, the methods of the present invention comprise administering a composition comprising at least one tetra-peptide of the present invention or a salt thereof.

According to certain embodiments, the methods comprise administering mixtures of peptides of the invention.

In some embodiments, the present invention provides the use of a peptide of the present invention or a salt thereof for the manufacture of a medicament for the treatment and/or prevention of a blood disease or disorder associated with glutathione dysregulation.

In some embodiments, a pharmaceutical composition is provided, comprising a peptide of the present invention or a salt thereof as active ingredient, for use in the treatment and/or prevention of a blood disease or disorder associated with glutathione dysregulation. Both chronic and acute uses of the pharmaceutical composition are within the scope of the present invention.

In some exemplary embodiments, the present invention provides the use of the peptide Cys-Lys-Met-Cys (SEQ ID NO: 1), in the treatment of a blood disorder associated with glutathione dysregulation.

In additional exemplary embodiments, the present invention provides the use of the peptide Cys-Met-Lys-Cys (SEQ ID NO: 2) in the treatment of a blood disorder associated with glutathione dysregulation.

In yet additional exemplary embodiments, the present invention provides the use of the peptide Cys-β-Ala-His-Cys (SEQ ID NO: 3) in the treatment of a blood disorder associated with glutathione dysregulation.

The amount (dosage) of the pharmaceutical composition of the present invention to be administered for the above indications, the administration regimes as well as their mode of application will depend both on characteristics of the treated individual (age, size, gender, etc.) as well as on parameters associated with the phenomena to be treated.

The present invention further provides kits. In some embodiments, a kit is provided for treating a disease or disorder associated with glutathione dysregulation. The aforementioned kit comprises a composition comprising at least one peptide of the present invention or a salt thereof, and may also include instructions for administering said composition to a subject in need thereof.

In some embodiment, the kit comprises means for administering the composition or compositions. For example, the kit may include a syringe.

The present invention further provides kits for preserving biological samples, comprising an additive composition comprising at least one peptide of the present invention, and storage means, for example, storage bags or vials.

In some embodiments, the kit comprises a composition comprising the at least one peptide (and optionally other active ingredients for preservation of biological samples) dissolved in a suitable solvent. In other embodiments, the kit comprises a first composition comprising the peptide (and optionally other active ingredients), e.g. as a dried powder, and a second composition comprising a solvent.

In some embodiments, the kit comprises storage means, such as bags or vials, said storage means contain therein an additive composition comprising the at least one peptide of the present invention.

The present invention further provides a preserved biological sample, such as a preserved blood sample, comprising the peptide of the present invention of a salt thereof In some embodiments, an isolated organ, tissue sample or a cell suspension are provided, in a medium containing the peptide of the present invention or salt thereof.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Effect of Peptides on Glutathione Status in Murine Erythrocytes Subjected to Oxidative Stress Peptide Synthesis:

The following peptides were synthesized by Solid Phase Peptide Synthesis (SPSS) using Fmoc strategy (purity >98%):

N-acetyl-Cys-Lys-Met-Cys-NH$_2$, designated herein as DY-65 (SEQ ID NO: 4);

N-acetyl-Cys-βAla-His-Cys-NH$_2$, designated herein as DY-66 (SEQ ID NO: 6); and N-acetyl-Cys-Met-Lys-Cys-NH$_2$, designated herein as DY-70 (SEQ ID NO: 5).

The peptides were prepared by SPSS in which there are repeated cycles of coupling-deprotection. The first stage of the technique consists of peptide chain assembly with protected amino acid derivatives on a polymeric support. The second stage of the technique is the cleavage of the peptide from the resin support with the concurrent cleavage of all side chain protecting groups to give the crude free peptide.

The free N-terminal amine of a solid-phase attached peptide is first coupled to a single N-protected amino acid unit. This unit is then deprotected, revealing a new N-terminal amine to which a further amino acid was attached. After cleavage from the resin, peptides are then purified by reverse phase HPLC using columns.

Fmoc Deprotection:

0.08 mmol of Fmoc-X-Wang resin is loaded into a fritted column equipped with a plastic cap. The resin is washed twice with 3 mL portions of dimethylformamide (DMF) for 1 minute each. Next, 3 ml of 20% piperidine in DMF is added and deprotection allowed to continue for 15 minutes. During this time, the column is gently swirled in order to assure a complete mixing. After the reaction is complete (in about 15 minutes), the reaction column is drained and the resin washed 4 times with 3 mL of DMF.

Amide Bond Coupling:

In a small vial, 3 equivalents of the Fmoc amino acid is preactivated by combining it with equal equivalents of O-Benzotriazole-N,N,N',N'-tetramethyl-uronium-hexafluoro-phosphate (HBTU), 6 equivalents of DIPEA (N,N'-diisopropylethylamine), and 3 mL of DMF. This solution is fully dissolved and then allowed to react for an additional 3-5 minutes. Then this coupling solution is added to the resin. The cap is placed on the reaction column and the resin slurry agitated every 2-3 minutes over a period of 20 minutes.

Cleavage:

In order to obtain the peptide in the free acid form, the ester linkage is cleaved using trifluoroacetic acid (TFA). The resin is treated with 2-3 mL of a solution of TFA and water in a ratio of 95:5. The resin is then agitated over a period of 25 minutes. The column is subsequently drained and the filtrated collected into a glass collection vessel. The material is then dried in diethyl ether and analyzed.

Hydrogen Peroxide Induced Oxidative Stress:

Murine erythrocytes ("Cells") were prepared by washing freshly harvested whole blood from mice three times in PBS. Cells were resuspended in DMEM at a concentration of $10^6$ per mL. All study conditions were evaluated in triplicate.

In Stage 1, cells were exposed to hydrogen peroxide in DMEM at a final concentration of 0, 300, 1000, and 2000 micromolar for 1 hour at 37° C. Cells were then washed three times in DMEM and allowed to recover at 37° C. for 1.5 hours. Cells were then pelleted by low-speed centrifugation and lysed in a buffer for measurement of GSH and GSSG. The GSH levels (micromolar) of the different groups are shown in FIG. 1A. "CON"=control (0 micromolar hydrogen peroxide); "H$_2$O$_2$"-hydrogen peroxide.

In Stage 2, three (3) concentrations of hydrogen peroxide were utilized to induce redox stress in murine erythrocytes. Prior to exposure to hydrogen peroxide, cells were randomly allocated to the following experimental groups:

1. Sham (no exposure to hydrogen peroxide; no drug)
2. Vehicle control (hydrogen peroxide; no drug)
3. DY-66 (1, 10, 100, 1000 μM)+hydrogen peroxide
4. DY-65 (1, 10, 100, 1000 μM)+hydrogen peroxide
5. DY-70 (1, 10, 100, 1000 μM)+hydrogen peroxide Cells at a concentration of $10^6$ per mL were incubated with vehicle DMEM (Groups 1 or 2) or Peptides (Groups 3-5) for 3 hours at 37° C. Thereafter, all cells were washed three times with DMEM and resuspended in vehicle DMEM (Group 1) or hydrogen peroxide in DMEM (Groups 2-5) for 1 hour at 37° C. Thereafter, all cells were washed three times with DMEM and resuspended in DMEM (Groups 1 and 2) or DMEM with Peptides (Groups 3-5) for 1.5 hours (at 37° C., $10^6$ per mL).

Cells were then pelleted, lysed, and processed for measurement of GSH and GSSG using a Glutathione Assay kit sold by Cayman (Chemical Item Number 703002). Data were expressed as micromoles of GSH or GSSG per 1 million erythrocytes.

Data analysis: All values were expressed as mean±standard deviation (SD) and standard error (SE) of n observations. The results were analyzed by one-way ANOVA followed by Tukey's post-hoc test for multiple comparisons. A p-value of less than 0.05 was considered significant.

Figure 1B:
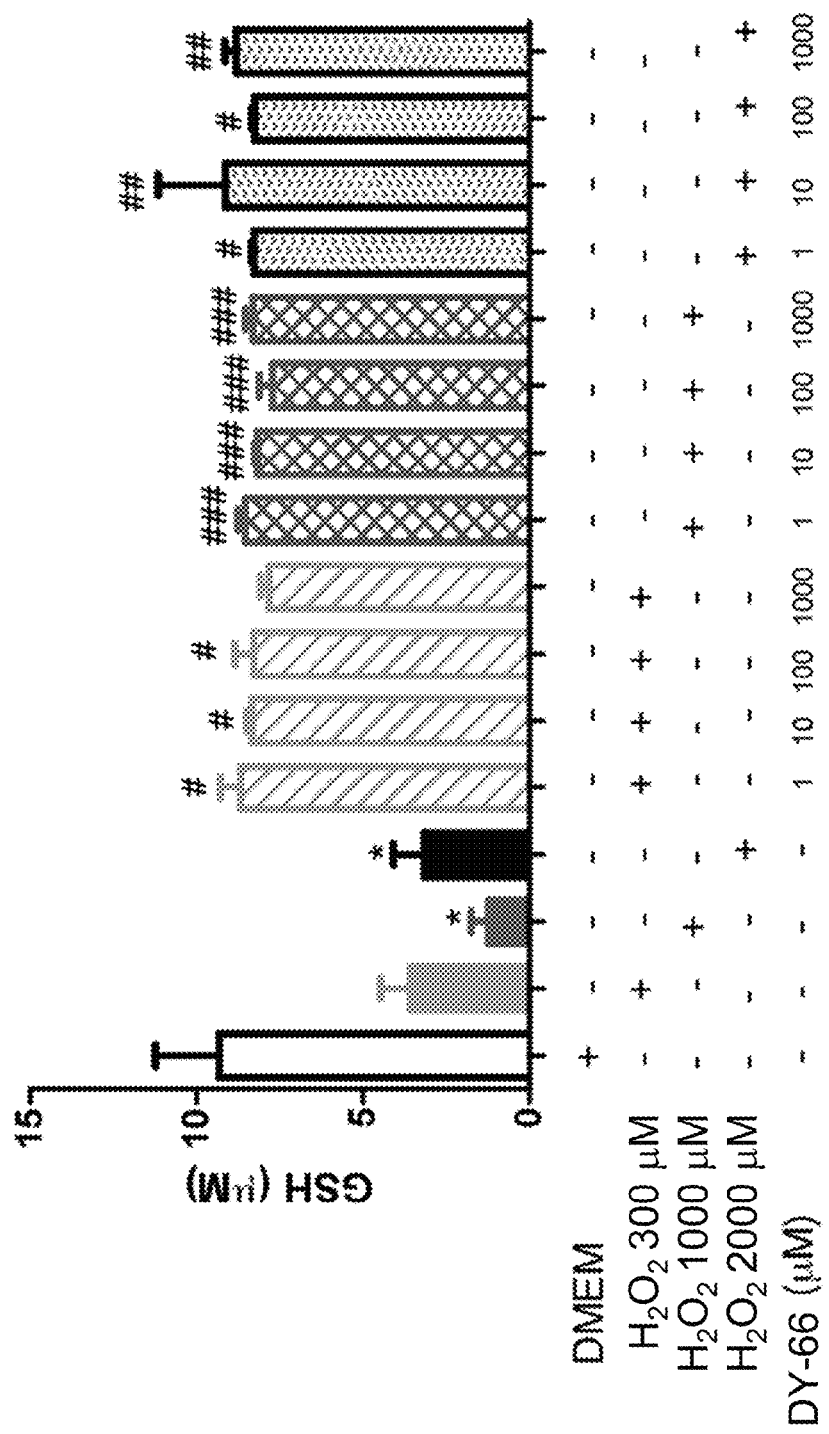
Figure 1C:
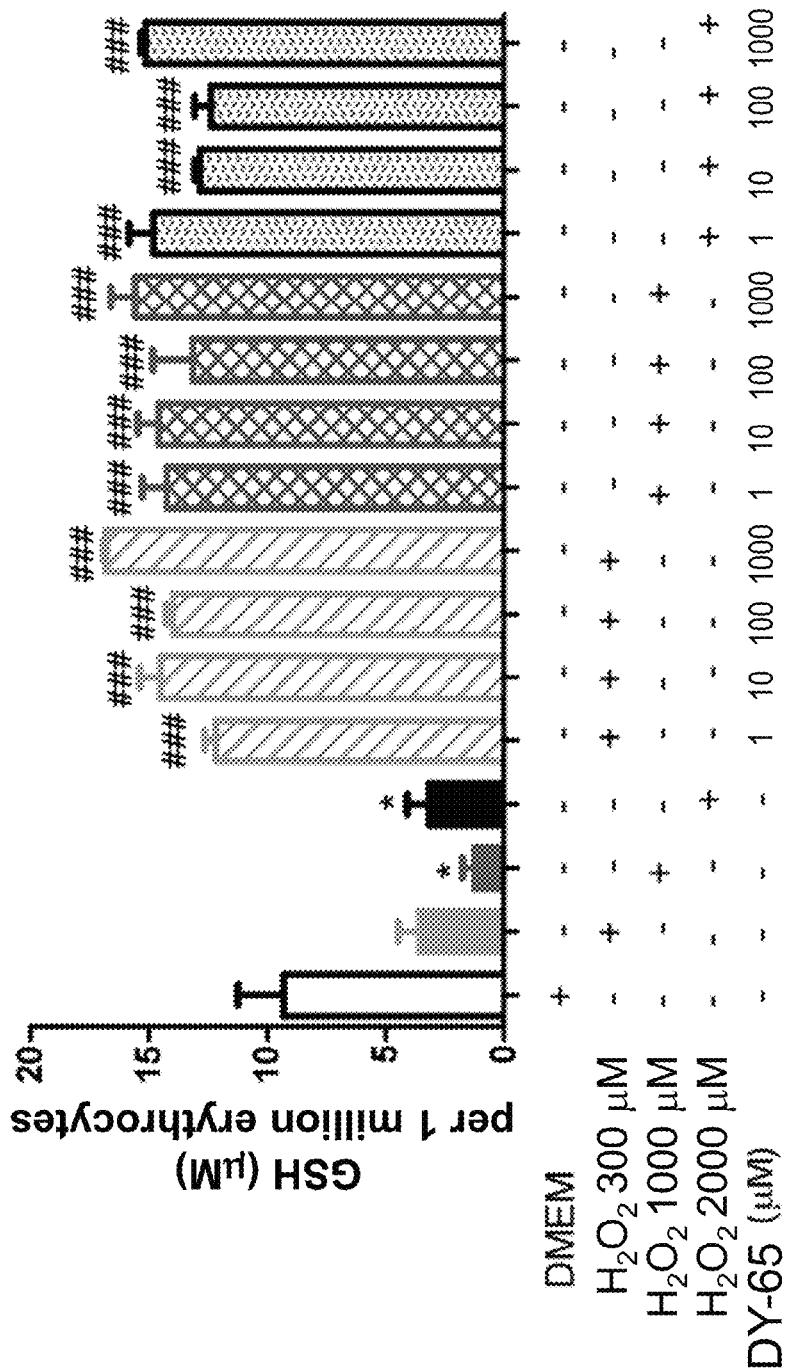
Figure 1D:
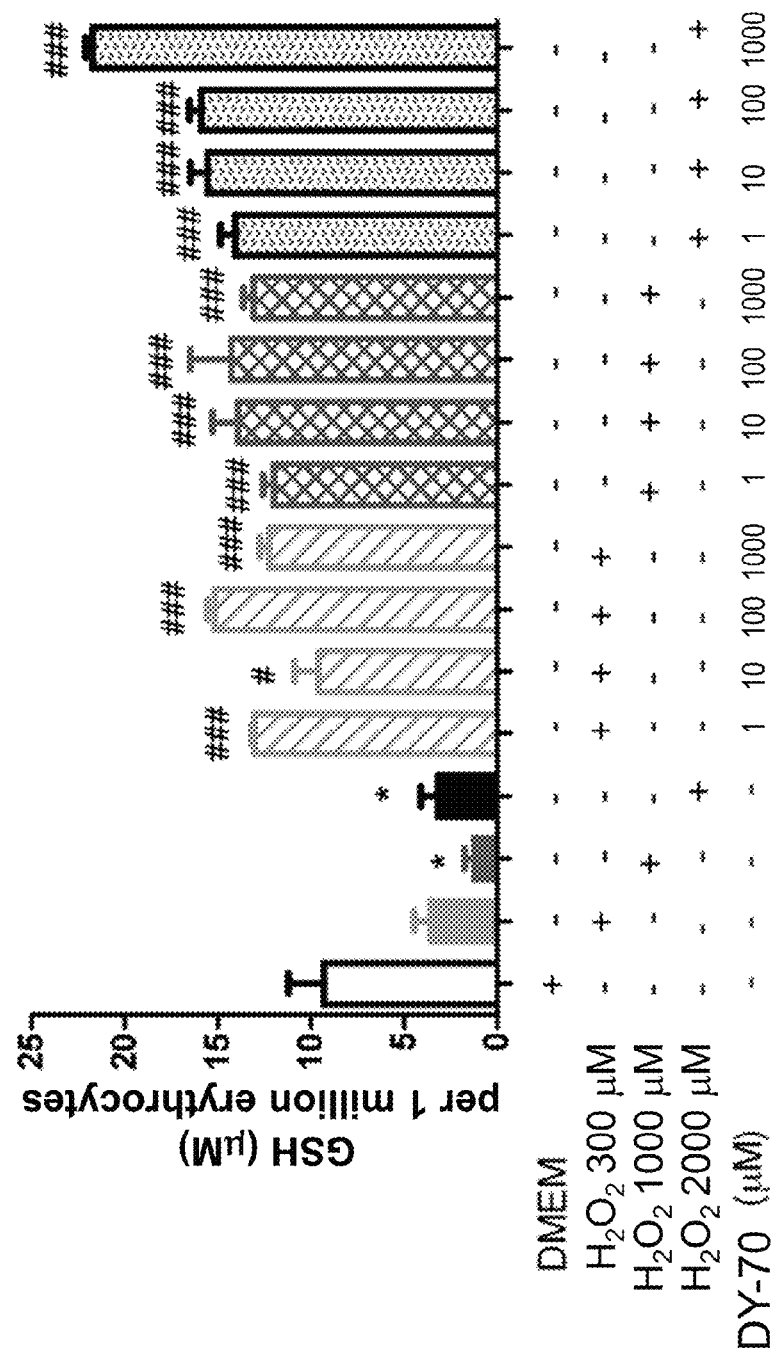

The GSH levels (micromolar, per 1 million erythrocytes) of the different groups are shown in FIG. 1B (DY-66), FIG. 1C (DY-65) and FIG. 1D (DY-70).

As seen in FIGS. 1A-D, erythrocytes were readily oxidized by exogenous application of hydrogen peroxide, as noted by the reduction in cellular GSH concentration. Incubation with all three peptides was protective of GSH concentration, even at the lowest concentration of peptide examined Example 2

Effect of DY-65 on GSH:GSSG Ratio in Murine Erythrocytes Subjected to Oxidative Stress The in vitro efficacy of peptide DY-65 in suppressing the decrease in the ratio of GSH to GSSG in murine erythrocytes exposed to hydrogen peroxide was tested.

Hydrogen Peroxide Induced Oxidative Stress.

Murine erythrocytes ("Cells") were prepared by washing freshly harvested whole blood from mice three times in PBS. Cells were resuspended in DMEM at a concentration of $10^6$ per mL. All study conditions were evaluated in triplicate.

Hydrogen peroxide (200 μM) was utilized to induce redox stress in murine erythrocytes ("Cells"). Prior to exposure to hydrogen peroxide, cells were randomly allocated to the following experimental groups:

1. Sham (no exposure to hydrogen peroxide; no drug)
   a. 2.5 h final incubation
2. Vehicle control (hydrogen peroxide; no drug)
   a. 1.0 h final incubation
   b. 1.5 h final incubation
   c. 2.0 h final incubation
   d. 2.5 h final incubation
3. DY-65 (5 μM)+hydrogen peroxide
   a. 1.0 h final incubation
   b. 1.5 h final incubation
   c. 2.0 h final incubation
   d. 2.5 h final incubation Cells at a concentration of $10^6$ per mL were incubated with vehicle DMEM (Groups 1 or 2) or peptide DY-65 (Group 3) for 3 hours at 37° C. Thereafter, cells were washed three times with DMEM and resuspended in vehicle DMEM (Group 1) or hydrogen peroxide in DMEM (Groups 2-3) for 1 hour at 37° C.

Thereafter, cells were washed three times with DMEM and resuspended in DMEM at 37° C., $10^6$ per mL, with peptide DY-65 (Group 3) or without peptide DY-65 (Groups 1-2). The duration of final incubation was 1.0, 1.5, 2.0, or 2.5 h. Cells were then pelleted, lysed, and processed for measurement of GSH and GSSG using a Glutathione Assay kit sold by Cayman (Chemical Item Number 703002). Data were expressed as micromoles of GSH or GSSG per 1 million erythrocytes.

Given 9 conditions, 3 replicates per condition, and 2 endpoints (GSH and GSSG), a total of 54 wells were incubated.

Data analysis. All values in the figure and text below were expressed as mean±standard deviation (SD) and standard error (SE) of n observations. The results were analyzed by one-way ANOVA followed by Tukey's post-hoc test for multiple comparisons. A p-value of less than 0.05 was considered significant.

Figure 2A:
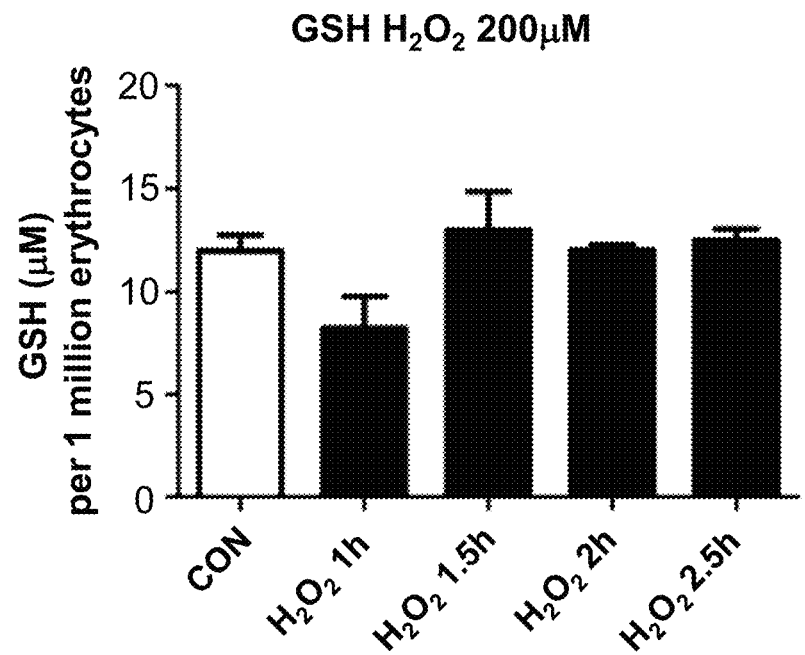
FIGS. 2A-2E. Effect of N-acetyl-Cys-Lys-Met-Cys-$NH_2$ (DY-65, SEQ ID NO: 4) on GSH:GSSG ratio in murine erythrocytes subjected to oxidative stress.
Figure 2B:
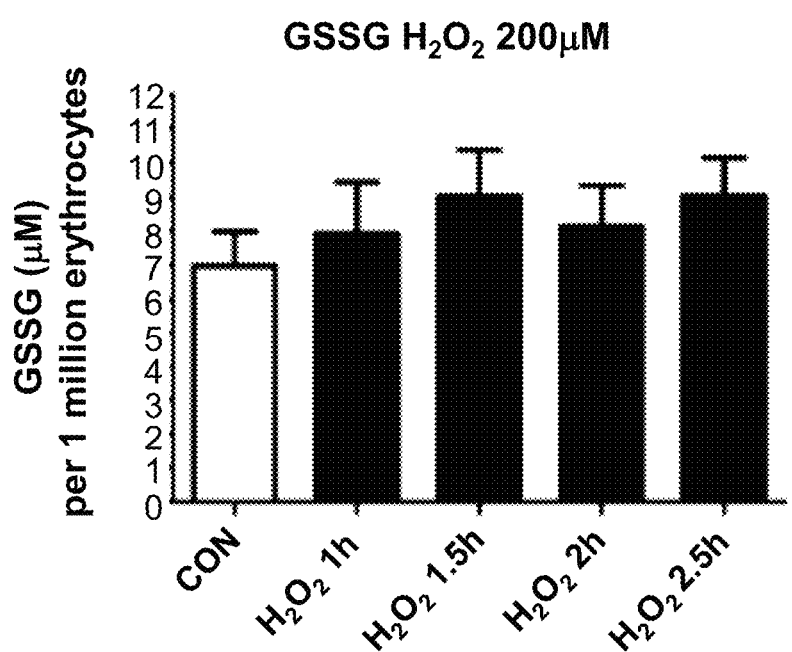

As seen in FIGS. 2A-B, erythrocytes were readily oxidized by exogenous application of hydrogen peroxide, as noted by the transient reduction in cellular GSH concentration and elevation in GSSG concentration appreciated at 1 h after exposure to hydrogen peroxide. Thereafter, cells recovered GSH concentrations (back to baseline). Conversely, exposure to redox stress increased GSSG at every timepoint examined (up to 2.5 h).

Figure 2C:
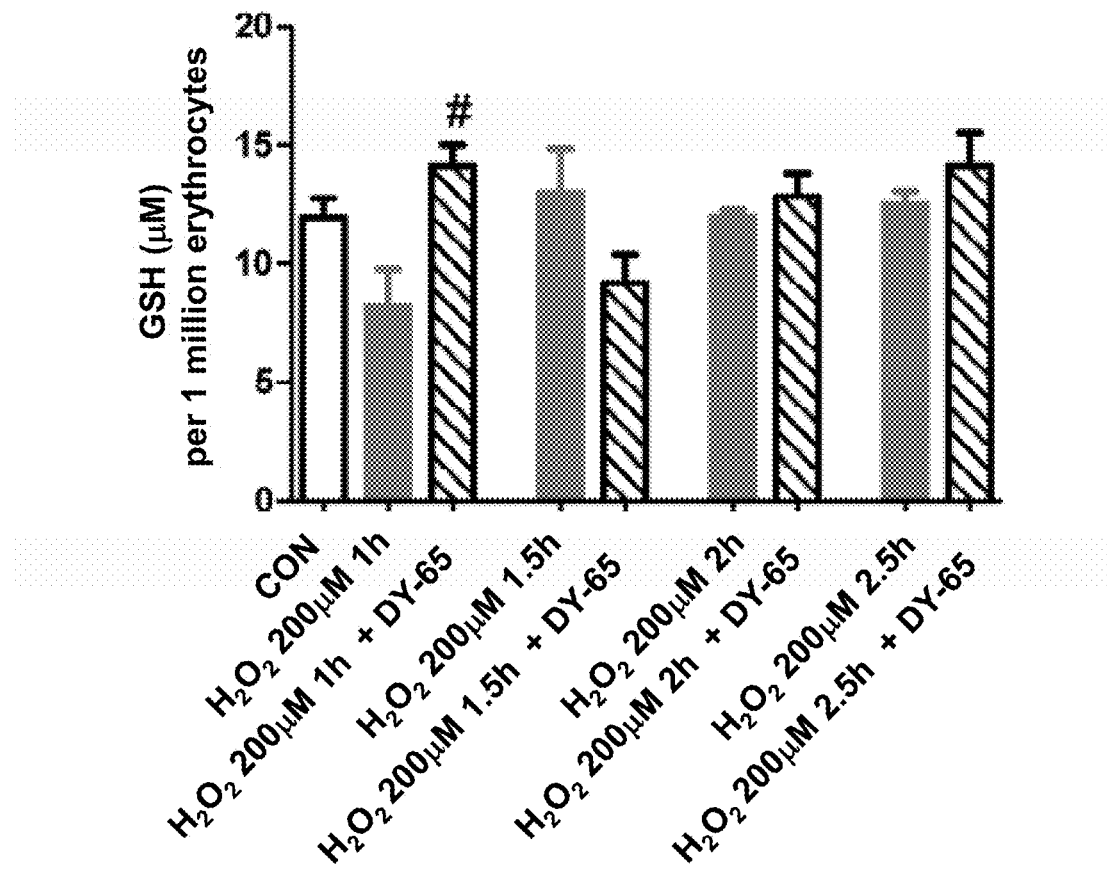
Figure 2D:
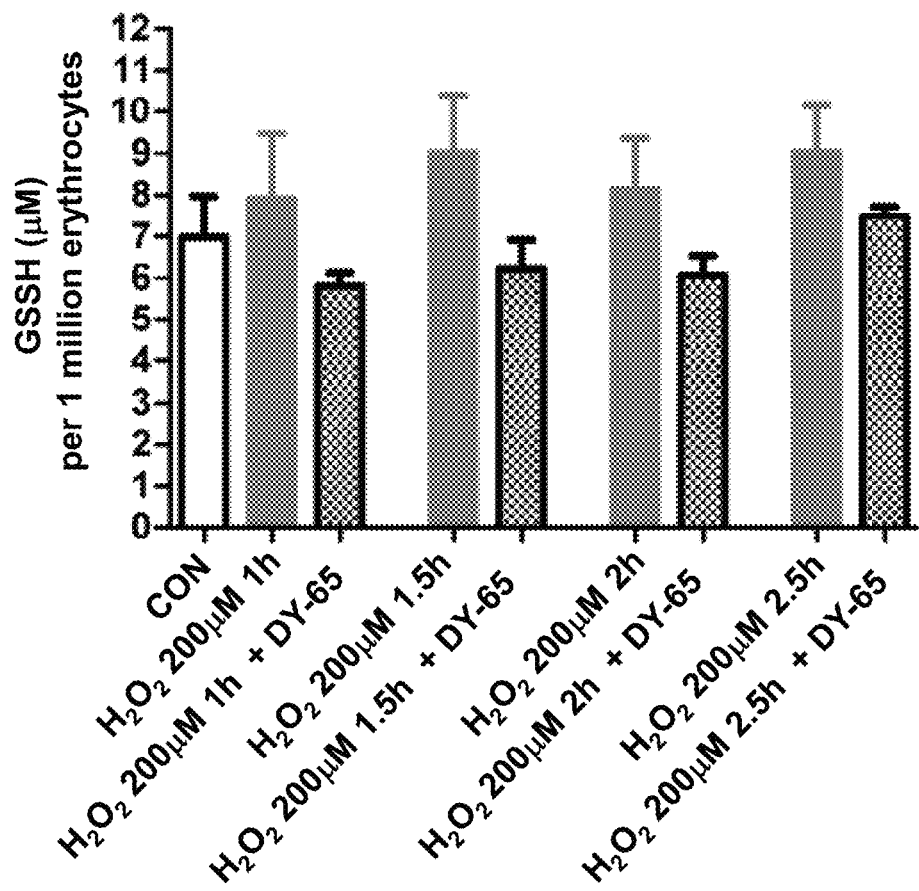
Figure 2E:
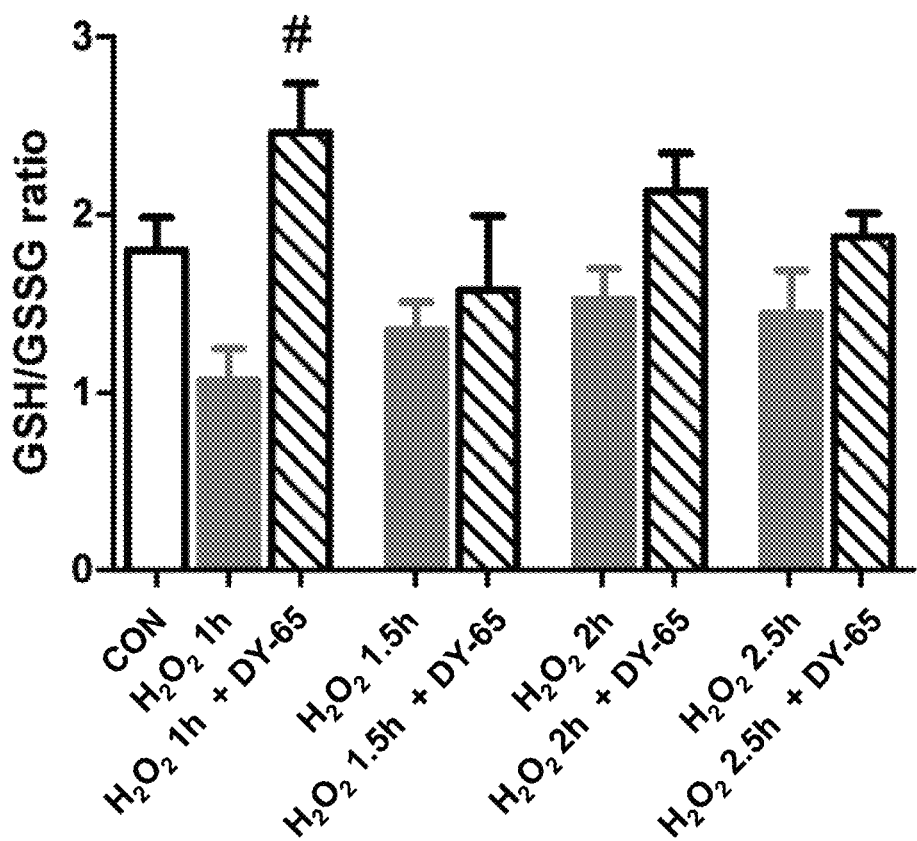

Incubation with DY-65 was completely protective of a hydrogen peroxide induced effect on GSH concentration at 1 h incubation, as shown in FIG. 2C. Treatment with DY-65 was uniformly effective in suppressing the elevation of GSSG in response to hydrogen peroxide (FIG. 2D). The ratio of GSH to GSSG was likewise informative, and demonstrated a clear benefit of DY-65 at the earliest measured time point (1 h post exposure), as shown in FIG. 2E.

Taken together, DY-65 is shown to increase GSH and decrease GSSG after cells have been exposed to hydrogen peroxide for 1 h duration, the peak timepoint at which oxidant stress is appreciated in this experimental model.

Example 3

In Vitro Effect of the Peptides on Red Blood Cells Obtained from Spherocytosis Patients Patients and Study Design:

Blood samples are obtained from 10 patients with spherocytosis, hereditary or acquired, from a cohort of patients treated in the Pediatric Hematology Unit at Emek Medical Center, Israel.

The following clinical data are recorded: age, gender, ethnic origin, type of spherocytosis (hereditary or sporadic), and time elapsed since the last blood transfusion and any drug treatment in the last several months.

Patients age: the study includes children from age 2 years and young adults. Both males and females are included.

Exclusion criteria: patients after splenectomy are not included in the first phase of the study. An extension study will be considered after analyzing the results.

Patients who received blood transfusions during 45 days before sampling are also excluded.

Patients that required drug treatment that included acetyl cysteine in the two weeks before the study are excluded.

Steroid treatment during 30 days before the sampling is also included as exclusion criteria. Pregnant women are also excluded.

Steady State Study:

Blood samples are obtained at least 60 days after the last blood transfusion or hemolytic crisis, even if blood transfusion was not required. Samples are not obtained during hemolytic crisis.

Blood samples are obtained in five EDTA vacutainer tubes (purple cup) for hematological analysis and another one Z. Serum Sep Clot Activator tube (Yellow cup) for biochemical analysis. The following analyses are performed soon after the collection of the samples (time 0):

Hematological analysis: Hgb level, Reticulocyte count, Mean Corpuscular Hemoglobin Concentration (MCHC), RBC morphology and Flow cytometry. For flow cytometry analysis the RBC are washed three times with Ca and Mg free phosphate buffered saline (PBS; Biological Industries, Kibbutz Beit HaEmek, Israel) and 5% Bovine Serum Albumin (BSA). 50 µl of RBC are needed for each analysis.

Biochemical analysis: Total and Indirect Bilirubin, LDH, K, and serum Iron.

Next, the five EDTA tubes (purple cup) are incubated with a tested peptide at four concentrations of the peptide, 1, 10, 50 and 100 µmolar—(micromolar), for 2 hours or 24 hours at 37° C. Another tube is incubated in the same conditions but without adding the peptide. After 1 hour, an aliquot is obtained from each tube and sent for hematological and biochemical analyses as described above. After 24 hours, an additional aliquot is obtained from each tube and the same hematological and biochemical analyses are performed.

The total amount of blood that is drawn is 12 ml: 2 ml in each of the five tubes with EDTA (purple cup) and 2 ml in the Serum Sep Clot Activator tube (Yellow cup). In patients aged 2 to 5 yrs, the total amount of blood is 9 ml (1.5 ml×5+1.5 ml×1).

Healthy Controls:

The same hematological and biochemical analyses are performed in 5 healthy controls.

Hemolytic Crises Study:

Similar laboratory tests are performed in patients with spherocytosis that are admitted to the pediatric ward because of hemolytic crisis during the study period, and eventually steroid treatment is prescribed for them. Blood samples are obtained before steroid treatment and after 24 hours of treatment.

Two blood samples are obtained in one EDTA vacutainer tube (purple cup) for hematological analysis and another Z. Serum Sep Clot Activator tube (Yellow cup) for biochemical analysis. The following analyses are performed:

Hematological analysis: Hgb level, Reticulocyte count, Mean Corpuscular Hemoglobin Concentration (MCHC), RBC morphology and Flow cytometry.

Biochemical analysis: Total and Indirect Bilirubin, LDH, K and Serum Iron.

Example 4

Effect of Peptides on GSH Level in Red Blood Cells from Thalassemia Patients and in a Mouse Model of Thalassemia Blood Collection and Cell Isolation:

Patients' blood (0.5 ml) samples are diluted with equal volume of $Ca^{++}$- and $Mg^{++}$-free Dulbecco's phosphate-buffered saline (PBS) (Biological Industries, Kibbutz BeitHaEmek, Israel), mixed with a double volume of 3% gelatin (Sigma, St. Louis, Mo.) in PBS and left to stand for 30 min at room temperature. The supernatant, containing RBC, but enriched for leukocytes and platelets, is collected, washed and used within 2 h of blood withdrawal.

Mice:

The founders of a thalassemic mouse colony are obtained. Heterozygotes (Hbb th3/+) mice, exhibit severe anemia (7 to 9 g/dL of Hb), abnormal RBC morphology, splenomegaly and hepatic iron deposition[15]. Animals are bred, four-month-old mice are intra-peritoneal injected with a tested peptide (150 mg/kg). Blood samples (20 µl) are collected from their tail vein prior and 2 h after treatment.

Assays for RBC Hemolysis and Phagocytosis:

RBC (5×10 6/ml) are suspended in a HEPES (10 mM) buffer containing 2.5 mM $CaCl_2$ and 170 mM NaCl, pH 7.4, and incubated overnight with various amounts of a tested peptide or N-acetyl cystein (NAC) for comparison. RBC are then centrifuged, resuspended in PBS and counted. Hemolysis is calculated as percentage of lysed RBC compared to the RBC input. The results are confirmed by spectrophotometric measurement of the Hb content in the hemolysate. To measure phagocytosis of RBC by macrophages, mononuclear blood cells obtained from normal donors are cultured according to the two-phase liquid culture procedures as described in Fibach et al. (1998) *Hemoglobin* 22; 445-458. Adherent macrophages from the first and second phases of the culture are collected by trypsinization, washed, resuspended in fresh alpha medium containing 10% fetal calf serum and re-cultured in multi-well dishes. Normal and thalassemic RBC are diluted to $5 \times 10^6$/ml with either PBS or thalassemic plasma and incubated for 24 h at 37° C. with or without a tested peptide or NAC. The RBC are then washed and placed in the macrophage-containing plates. After overnight incubation, the non-phagocytosed RBC are harvested and counted microscopically using a hemocytometer. The extent of phagocytosis is calculated as the percent of phagocytosed RBC per the RBC input.

The modulation of GSH levels is first tested in thalassemic red blood cells (RBC). These RBC are collected, washed and incubated at $1-2 \times 10^6$/ml for 1 h in the absence or presence of either 1 mM of a tested peptide or N-acetyls cysteine (NAC) for comparison, and GSH is assessed at different time points.

To determine in vitro effects of the peptides on GSH levels in other blood cell types, 1 mM of a tested peptide is added to a suspension of RBC, platelets and PMN separated on gelatin. After 30 min incubation, the cells are washed, and their GSH content determined by flow cytometry.

Example 5

Protection of RBC from Lysis and Phagocytosis

To study the effect of in vitro treatment with the peptides on hemolysis and phagocytosis the following experiments are carried out:

Heparinized thalassemic RBC diluted in phosphate-buffered saline are incubated overnight with various concentrations of NAC or the tested peptide. The cells are then centrifuged, the RBC in the pellet are resuspended in PBS and counted.

Normal and thalassemic RBC are washed, diluted and pre-incubated for 24 h with either PBS or thalassemic plasma with or without a tested peptide or NAC. The RBC are then washed and incubated overnight with macrophages, followed by counting the non phagocytosed RBC.

Example 6

In Vivo Effects of the Peptides

The effect of the peptides is determined in thalassemic mice. A tested peptide is injected i.p. at 150 mg/kg; blood samples are drawn prior to and after 2-h treatment, and RBC, platelets and/or PMN are analyzed for ROS and GSH.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method for treating a blood disorder associated with glutathione dysregulation, the method comprising administering to a subject suffering from a blood disorder associated with glutathione dysregulation a pharmaceutical composition comprising as an active ingredient at least one peptide or a salt thereof having the amino acid sequence selected from the group consisting of:

Cys-Lys-Met-Cys, (SEQ ID NO: 1)

Cys-Met-Lys-Cys; (SEQ ID NO: 2)
and

Cys-β-Ala-His-Cys. (SEQ ID NO: 3)

2. The method of claim 1, wherein the blood disorder is manifested by hemolytic anemia.

3. The method of claim 1, wherein the blood disorder is an intrinsic abnormality of red blood cells or a disorder extrinsic to red blood cells.

4. The method of claim 3, wherein the intrinsic abnormality of red blood cells is selected from the group consisting of a red blood cell membrane disorder, a disorder of hemoglobin production (hemoglobinopathy) and a disorder of red blood cell metabolism.

5. The method of claim 4, wherein the red blood cell membrane disorder is selected from the group consisting of hereditary spherocytosis, hereditary elliptocytosis and paroxysmal nocturnal hemoglobinuria.

6. The method of claim 4, wherein the disorder of hemoglobin production (hemoglobinopathy) is a thalassemia selected from the group consisting of α-thalassemia and β-thalassemia.

7. The method of claim 4, wherein the disorder of hemoglobin production (hemoglobinopathy) is a variant hemoglobin syndrome.

8. The method of claim 7, wherein the variant hemoglobin syndrome is selected from the group consisting of a sickle-cell disease, HbC disease, HbE homozygosity (HbE disease) and HbE heterozygosity.

9. The method of claim 4, wherein the disorder of red blood cell metabolism is glucose-6-phosphate dehydrogenase (G6PD) deficiency.

10. The method of claim 3, wherein the disorder extrinsic to red blood cells is a disorder resulting from an immunologic abnormality, an infection or a toxic substance.

11. The method of claim 3, wherein the disorder extrinsic to red blood cells is hemolytic uremic syndrome or autoimmune hemolytic anemia.

12. The method of claim 1, wherein the blood disorder is idiopathic thrombocytopenic purpura.

13. The method of claim 1, wherein the peptide administered as the active ingredient is of 4-10 amino acids.

14. The method of claim 1, wherein the peptide further comprises at least one modification selected from the group consisting of an amino-terminal modification and a carboxy terminal modification.

15. The method of claim 14, wherein the amino terminal modification is an amino terminal blocking group.

16. The method of claim 15, wherein the amino-terminal blocking group is an alkyl group or an acyl group.

17. The method of claim 16, wherein the amino-terminal blocking group is an acetyl group.

18. The method of claim 14, wherein the amino terminal modification is a permeability-enhancing moiety selected from the group consisting of lipids, fatty acids, steroids and bulky aromatic or aliphatic compounds.

19. The method of claim 14, wherein the carboxy terminal modification is a carboxy terminal blocking group.

20. The method of claim 19, wherein the carboxy terminal blocking group is selected from the group consisting of an amide, ester and alcohol.

21. The method of claim 20, wherein the carboxy terminal blocking group is an amide group.

22. The method of claim 1, further comprising administering N-acetylcysteine (NAC) to the subject in need thereof.

23. The method of claim 1, wherein the peptide is a tetra-peptide.

* * * * *

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Peptide

<400> SEQUENCE: 1

Cys Lys Met Cys
1

<210> SEQ ID NO 2
<211> LENGTH: 4
<212> TYPE: PRT
<213> ORGANISM: Artificial Sequence
<220> FEATURE:
```

```
<223> OTHER INFORMATION: Peptide

<400> SEQUENCE: 2

Cys Met Lys Cys
1

<210> SEQ ID NO 3
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (2)..(2)
<223> OTHER INFORMATION: X= beta-alanine

<400> SEQUENCE: 3

Cys Xaa His Cys
1

<210> SEQ ID NO 4
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (4)..(4)
<223> OTHER INFORMATION: C-terminal amide group

<400> SEQUENCE: 4

Cys Lys Met Cys
1

<210> SEQ ID NO 5
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (4)..(4)
<223> OTHER INFORMATION: C-terminal amide group

<400> SEQUENCE: 5

Cys Met Lys Cys
1

<210> SEQ ID NO 6
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
```

```
<222> LOCATION: (2)..(2)
<223> OTHER INFORMATION: X= beta-alanine
<220> FEATURE:
<221> NAME/KEY: MISC_FEATURE
<222> LOCATION: (4)..(4)
<223> OTHER INFORMATION: C-terminal amide group

<400> SEQUENCE: 6

Cys Xaa His Cys
1

<210> SEQ ID NO 7
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Optional N-terminal modification
<220> FEATURE:
<221> NAME/KEY: MISC_FEATURE
<222> LOCATION: (4)..(4)
<223> OTHER INFORMATION: Optional C-terminal modification

<400> SEQUENCE: 7

Cys Lys Met Cys
1

<210> SEQ ID NO 8
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Optional N-terminal modification
<220> FEATURE:
<221> NAME/KEY: MISC_FEATURE
<222> LOCATION: (4)..(4)
<223> OTHER INFORMATION: Optional C-terminal modification

<400> SEQUENCE: 8

Cys Met Lys Cys
1

<210> SEQ ID NO 9
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Optional N-terminal modification
<220> FEATURE:
<221> NAME/KEY: MISC_FEATURE
<222> LOCATION: (2)..(2)
<223> OTHER INFORMATION: X= beta-alanine
<220> FEATURE:
<221> NAME/KEY: MISC_FEATURE
<222> LOCATION: (4)..(4)
<223> OTHER INFORMATION: Optional C-terminal modification

<400> SEQUENCE: 9

Cys Xaa His Cys
1
```